(12) United States Patent
Rotem-Yehudar et al.

(10) Patent No.: US 8,686,119 B2
(45) Date of Patent: Apr. 1, 2014

(54) VARIANTS OF HUMANIZED IMMUNOMODULATORY MONOCLONAL ANTIBODIES

(75) Inventors: Rinat Rotem-Yehudar, Tel Aviv (IL); Michael Schickler, Mazkeret Batya (IL)

(73) Assignee: CureTech Ltd., Yavne (IL)

( * ) Notice: Subject to any disclaimer, the term of this patent is extended or adjusted under 35 U.S.C. 154(b) by 0 days.

(21) Appl. No.: 13/556,018

(22) Filed: Jul. 23, 2012

(65) Prior Publication Data
US 2013/0022595 A1 Jan. 24, 2013

Related U.S. Application Data

(60) Provisional application No. 61/511,055, filed on Jul. 24, 2011.

(51) Int. Cl.
*C07K 16/28* (2006.01)
*A61K 39/395* (2006.01)

(52) U.S. Cl.
USPC ............ 530/387.3; 530/388.1; 530/388.73; 424/133.1; 424/141.1; 424/153.1

(58) Field of Classification Search
None
See application file for complete search history.

(56) References Cited

U.S. PATENT DOCUMENTS

| | | | |
|---|---|---|---|
| 5,225,539 A | 7/1993 | Winter | 530/387.3 |
| 5,897,862 A | 4/1999 | Hardy et al. | 424/153.1 |
| 6,884,879 B1 * | 4/2005 | Baca et al. | 536/23.53 |
| 7,332,582 B2 | 2/2008 | Hardy et al. | 530/387.3 |
| 7,695,715 B2 | 4/2010 | Hardy et al. | 424/130.1 |
| 2003/0026800 A1 | 2/2003 | Hardy et al. | 424/132.1 |
| 2003/0027994 A1 * | 2/2003 | Anderson et al. | 530/388.15 |
| 2008/0025980 A1 * | 1/2008 | Hardy et al. | 424/136.1 |

FOREIGN PATENT DOCUMENTS

| | | |
|---|---|---|
| WO | WO 00/58363 | 10/2000 |
| WO | WO 03/099196 A2 | 12/2003 |
| WO | WO 2009/101611 A1 | 8/2009 |

OTHER PUBLICATIONS

Paul, Fundamental Immunology, 3rd Edition, 1993, pp. 292-295.*
Rudikoff et al., Proc. Nat'l Acad. Sci. USA 1982; 79:1979-83.*
Brown et al., J. Immunol. 1996; 156(9):3285-91.*
International Search Report, application No. PCT/IL2012/050267 (Oct. 17, 2012).
Benson Jr., et al., "The PD-1/PD-L1 axis modulates the natural killer cell versus multiple myeloma effect: a therapeutic target for CT-011, a novel monoclonal anti-PD-1 antibody," Blood, 116(13):2286-2294 (2010).
Berger, Raanan et al., (2008) Phase I Safety and Pharmacokinetic Study of CT-011, a Humanized Antibody Interacting with PD-1, in Patients with Advanced Hematologic Malignancies. *Clin Cancer Res* 14(10):3044-3051.
Chothia, Cyrus et al., (1985) Domain association in immunoglobulin molecules. The packing of variable domains. *J Mol Biol* 186(3):651-663.
Fang, Qiang et al., (1994) Human rheumatoid factors with restrictive specificity for rabbit immunoglobulin G: auto- and multi-reactivity, diverse VH gene segment usage and preferential usage of V lambda IIIb. *J Exp Med* 179(5):1445-1456.
Hardy, Britta et al., (1997) A lymphocyte-activating monoclonal antibody induces regression of human tumors in severe combined immunodeficient mice. *Proc Natl Acad Sci USA* 94(11):5756-5760.
Hardy, Britta et al., (1997) Immune stimulatory and anti-tumor properties of anti-CD3 and BAT monoclonal antibodies: a comparative study. *Hum Antibodies* 8(2):95-98.
Hardy, Britta et al., (2001) Treatment with BAT monoclonal antibody decreases tumor burden in a murine model of leukemia/lymphoma. *Int J Oncol* 19(5):897-902 (2001).
Huang, Lihua et al., (2005) In vivo deamidation characterization of monoclonal antibody by LC/MS/MS. Anal Chem 77(5):1432-1439.
Marks, James D. et al., (1991) By-passing immunization. Human antibodies from V-gene libraries displayed on phage. *J Mol Biol* 222(3):581-597.
Novotny, Jiri and Haber, Edgar (1985) Structural invariants of antigen binding: comparison of immunoglobulin VL-VH and VL-VL domain dimers*Proc Natl Acad Sci USA* 82(14):4592-4596.
Quaglino, Elena et al., (2005) The adjuvant activity of BAT antibody enables DNA vaccination to inhibit the progression of established autochthonous Her-2/neu carcinomas in BALB/c mice. *Vaccine* 23(25):3280-3287.
Raiter, Annat et al., (2000) CD4+ T lymphocytes as a primary cellular target for BAT mAb stimulation. *Int Immunol* 12(11):1623-1628.

* cited by examiner

*Primary Examiner* — Sheela J Huff
*Assistant Examiner* — Jessica H Roark
(74) *Attorney, Agent, or Firm* — Winston & Strawn LLP

(57) ABSTRACT

The present invention relates to humanized monoclonal antibodies, pharmaceutical compositions that include the same, and use thereof for the treatment of a variety of indications, particularly cancer and immunodeficiency disorders. In particular, the present invention provides modified antibodies or fragments thereof having specific amino acid modifications compared to the humanized monoclonal immunomodulatory antibody termed hBAT-1.

3 Claims, 1 Drawing Sheet

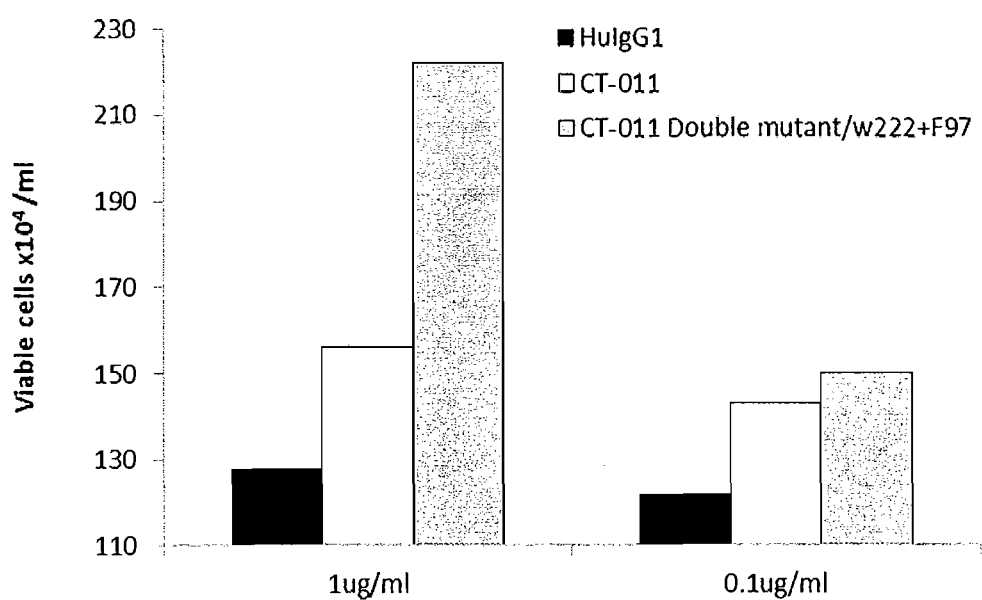

SEQUENCE LISTING

```
<160> NUMBER OF SEQ ID NOS: 31

<210> SEQ ID NO 1
<211> LENGTH: 106
<212> TYPE: PRT
<213> ORGANISM: Artificial sequence
<220> FEATURE:
<223> OTHER INFORMATION: Synthetic peptide

<400> SEQUENCE: 1

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 2
<211> LENGTH: 106
<212> TYPE: PRT
<213> ORGANISM: Artificial sequence
<220> FEATURE:
<223> OTHER INFORMATION: Synthetic peptide

<400> SEQUENCE: 2

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Tyr Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 3
<211> LENGTH: 106
<212> TYPE: PRT
<213> ORGANISM: Artificial sequence
<220> FEATURE:
<223> OTHER INFORMATION: Synthetic peptide
```

-continued

<400> SEQUENCE: 3

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 4
<211> LENGTH: 107
<212> TYPE: PRT
<213> ORGANISM: Artificial sequence
<220> FEATURE:
<223> OTHER INFORMATION: Synthetic peptide

<400> SEQUENCE: 4

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu
                85                  90                  95

Thr Phe Gly Gly Gly Thr Lys Leu Glu Ile Lys
            100                 105

<210> SEQ ID NO 5
<211> LENGTH: 117
<212> TYPE: PRT
<213> ORGANISM: Artificial sequence
<220> FEATURE:
<223> OTHER INFORMATION: Synthetic peptide

<400> SEQUENCE: 5

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

```
Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115

<210> SEQ ID NO 6
<211> LENGTH: 117
<212> TYPE: PRT
<213> ORGANISM: Artificial sequence
<220> FEATURE:
<223> OTHER INFORMATION: Synthetic peptide

<400> SEQUENCE: 6

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Ser Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
            100                 105                 110

Val Thr Val Ser Ser
        115

<210> SEQ ID NO 7
<211> LENGTH: 117
<212> TYPE: PRT
<213> ORGANISM: Artificial sequence
<220> FEATURE:
<223> OTHER INFORMATION: Synthetic peptide

<400> SEQUENCE: 7

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
            100                 105                 110

Val Thr Val Ser Ser
        115
```

<210> SEQ ID NO 8
<211> LENGTH: 117
<212> TYPE: PRT
<213> ORGANISM: Artificial sequence
<220> FEATURE:
<223> OTHER INFORMATION: Synthetic peptide

<400> SEQUENCE: 8

```
Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115
```

<210> SEQ ID NO 9
<211> LENGTH: 117
<212> TYPE: PRT
<213> ORGANISM: Artificial sequence
<220> FEATURE:
<223> OTHER INFORMATION: Synthetic peptide

<400> SEQUENCE: 9

```
Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Ala Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115
```

<210> SEQ ID NO 10
<211> LENGTH: 107
<212> TYPE: PRT
<213> ORGANISM: Artificial sequence
<220> FEATURE:
<223> OTHER INFORMATION: Synthetic peptide

```
<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 11
<211> LENGTH: 213
<212> TYPE: PRT
<213> ORGANISM: Artificial sequence
<220> FEATURE:
<223> OTHER INFORMATION: Synthetic peptide

<400> SEQUENCE: 11

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
            85                  90                  95

Phe Gly Gly Gly Thr Lys Leu Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
    195                 200                 205

Asn Arg Gly Glu Cys
    210

<210> SEQ ID NO 12
<211> LENGTH: 330
<212> TYPE: PRT
<213> ORGANISM: Artificial sequence
```

<220> FEATURE:
<223> OTHER INFORMATION: Synthetic peptide

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 447
<212> TYPE: PRT
<213> ORGANISM: Artificial sequence
<220> FEATURE:
<223> OTHER INFORMATION: Synthetic peptide

<400> SEQUENCE: 13

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
        420                 425                 430
His Asn His Tyr Thr Gln Lys Ser Leu Ser Leu Ser Pro Gly Lys
        435                 440                 445

<210> SEQ ID NO 14
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (93)..(93)
<223> OTHER INFORMATION: Xaa = Ala, Leu or Val

<400> SEQUENCE: 14

Glu Ile Val Leu Thr Gln Ser Pro Ser Ser Leu Ser Ala Ser Val Gly
1               5                   10                  15
Asp Arg Val Thr Ile Thr Cys Ser Ala Arg Ser Ser Val Ser Tyr Met
            20                  25                  30
His Trp Phe Gln Gln Lys Pro Gly Lys Ala Pro Lys Leu Trp Ile Tyr
        35                  40                  45
Arg Thr Ser Asn Leu Ala Ser Gly Val Pro Ser Arg Phe Ser Gly Ser
    50                  55                  60
Gly Ser Gly Thr Ser Tyr Cys Leu Thr Ile Asn Ser Leu Gln Pro Glu
65                  70                  75                  80
Asp Phe Ala Thr Tyr Tyr Cys Gln Gln Arg Ser Ser Xaa Pro Leu Thr
                85                  90                  95
Phe Gly Gly Gly Thr Lys Leu Glu Ile Lys
            100                 105

<210> SEQ ID NO 15
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (97)..(97)
<223> OTHER INFORMATION: Xaa = Ala, Leu or Val

<400> SEQUENCE: 15

Glu Ile Val Leu Thr Gln Ser Pro Ser Ser Leu Ser Ala Ser Val Gly
1               5                   10                  15
Asp Arg Val Thr Ile Thr Cys Ser Ala Arg Ser Ser Val Ser Tyr Met
            20                  25                  30
His Trp Phe Gln Gln Lys Pro Gly Lys Ala Pro Lys Leu Trp Ile Tyr
        35                  40                  45
Arg Thr Ser Asn Leu Ala Ser Gly Val Pro Ser Arg Phe Ser Gly Ser
    50                  55                  60
Gly Ser Gly Thr Ser Tyr Cys Leu Thr Ile Asn Ser Leu Gln Pro Glu
65                  70                  75                  80
Asp Phe Ala Thr Tyr Tyr Cys Gln Gln Arg Ser Ser Phe Pro Leu Thr
                85                  90                  95
Xaa Gly Gly Gly Thr Lys Leu Glu Ile Lys
            100                 105
```

```
<210> SEQ ID NO 16
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (93)..(93)
<223> OTHER INFORMATION: Xaa = Ala, Leu or Val

<400> SEQUENCE: 16

Glu Ile Val Leu Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Xaa Pro Leu Thr
                85                  90                  95

Phe Gly Gly Gly Thr Lys Leu Glu Ile Lys
            100                 105

<210> SEQ ID NO 17
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (97)..(97)
<223> OTHER INFORMATION: Xaa = Ala, Leu or Val

<400> SEQUENCE: 17

Glu Ile Val Leu Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Xaa Gly Gly Gly Thr Lys Leu Glu Ile Lys
            100                 105

<210> SEQ ID NO 18
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (93)..(93)
<223> OTHER INFORMATION: Xaa = Ala, Leu or Val
```

-continued

```
<400> SEQUENCE: 18

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Xaa Pro Leu Thr
                85                  90                  95

Phe Gly Gly Gly Thr Lys Leu Glu Ile Lys
            100                 105

<210> SEQ ID NO 19
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (97)..(97)
<223> OTHER INFORMATION: Xaa = Ala, Leu or Val

<400> SEQUENCE: 19

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Xaa Gly Gly Gly Thr Lys Leu Glu Ile Lys
            100                 105

<210> SEQ ID NO 20
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (93)..(93)
<223> OTHER INFORMATION: Xaa = Ala, Leu or Val

<400> SEQUENCE: 20

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45
```

Arg Thr Ser Asn Leu Ala Ser Gly Val Pro Ser Arg Phe Ser Gly Ser
            50                  55                  60

Gly Ser Gly Thr Asp Tyr Cys Leu Thr Ile Asn Ser Leu Gln Pro Glu
 65                  70                  75                  80

Asp Phe Ala Thr Tyr Tyr Cys Gln Gln Arg Ser Ser Xaa Pro Leu Thr
                 85                  90                  95

Phe Gly Gly Gly Thr Lys Leu Glu Ile Lys
            100                 105

<210> SEQ ID NO 21
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (97)..(97)
<223> OTHER INFORMATION: Xaa = Ala, Leu or Val

<400> SEQUENCE: 21

Glu Ile Val Leu Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
                 20                  25                  30

His Trp Phe Gln Gln Lys Pro Gly Lys Ala Pro Lys Leu Trp Ile Tyr
             35                  40                  45

Arg Thr Ser Asn Leu Ala Ser Gly Val Pro Ser Arg Phe Ser Gly Ser
         50                  55                  60

Gly Ser Gly Thr Asp Tyr Cys Leu Thr Ile Asn Ser Leu Gln Pro Glu
 65                  70                  75                  80

Asp Phe Ala Thr Tyr Tyr Cys Gln Gln Arg Ser Ser Phe Pro Leu Thr
                 85                  90                  95

Xaa Gly Gly Gly Thr Lys Leu Glu Ile Lys
            100                 105

<210> SEQ ID NO 22
<211> LENGTH: 106
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (93)..(93)
<223> OTHER INFORMATION: Xaa = Ala, Leu or Val
<220> FEATURE:
<221> NAME/KEY: MISC_FEATURE
<222> LOCATION: (97)..(97)
<223> OTHER INFORMATION: Xaa = Ala, Leu or Val

<400> SEQUENCE: 22

Glu Ile Val Leu Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
                 20                  25                  30

His Trp Phe Gln Gln Lys Pro Gly Lys Ala Pro Lys Leu Trp Ile Tyr
             35                  40                  45

Arg Thr Ser Asn Leu Ala Ser Gly Val Pro Ser Arg Phe Ser Gly Ser
         50                  55                  60

Gly Ser Gly Thr Ser Tyr Cys Leu Thr Ile Asn Ser Leu Gln Pro Glu
 65                  70                  75                  80

```
Asp Phe Ala Thr Tyr Tyr Cys Gln Gln Arg Ser Ser Xaa Pro Leu Thr
                85                  90                  95

Xaa Gly Gly Gly Thr Lys Leu Glu Ile Lys
            100                 105
```

<210> SEQ ID NO 23
<211> LENGTH: 106
<212> TYPE: PRT
<213> ORGANISM: Artificial sequence
<220> FEATURE:
<223> OTHER INFORMATION: Synthetic peptide

<400> SEQUENCE: 23

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Phe Gln Gln Lys Pro Gly Lys Ala Pro Lys Leu Trp Ile Tyr
            35                  40                  45

Arg Thr Ser Asn Leu Ala Ser Gly Val Pro Ser Arg Phe Ser Gly Ser
        50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Ala Pro Leu Thr
                85                  90                  95

Ala Gly Gly Gly Thr Lys Leu Glu Ile Lys
            100                 105
```

<210> SEQ ID NO 24
<211> LENGTH: 117
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (107)..(107)
<223> OTHER INFORMATION: Xaa = Ala, Leu, Tyr or Val

<400> SEQUENCE: 24

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Xaa Gly Gln Gly Thr Leu
            100                 105                 110

Val Thr Val Ser Ser
        115
```

<210> SEQ ID NO 25
<211> LENGTH: 117
<212> TYPE: PRT
<213> ORGANISM: Artificial sequence -continued

```
<220> FEATURE:
<223> OTHER INFORMATION: Synthetic peptide
<220> FEATURE:
<221> NAME/KEY: MISC_FEATURE
<222> LOCATION: (107)..(107)
<223> OTHER INFORMATION: Xaa = Ala, Leu, Tyr or Val

<400> SEQUENCE: 25

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Ser Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Xaa Gly Gln Gly Thr Leu
            100                 105                 110

Val Thr Val Ser Ser
        115

<210> SEQ ID NO 26
<211> LENGTH: 117
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (107)..(107)
<223> OTHER INFORMATION: Xaa = Ala, Leu, Tyr or Val

<400> SEQUENCE: 26

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Gln Trp Met
            35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Xaa Gly Gln Gly Thr Leu
            100                 105                 110

Val Thr Val Ser Ser
        115

<210> SEQ ID NO 27
<211> LENGTH: 117
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MISC_FEATURE
<222> LOCATION: (107)..(107)
<223> OTHER INFORMATION: Xaa = Ala, Leu, Tyr or Val

<400> SEQUENCE: 27

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Xaa Gly Gln Gly Thr Leu
            100                 105                 110

Val Thr Val Ser Ser
        115

<210> SEQ ID NO 28
<211> LENGTH: 117
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (107)..(107)
<223> OTHER INFORMATION: Xaa = Ala, Leu, Tyr or Val

<400> SEQUENCE: 28

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Ala Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Xaa Gly Gln Gly Thr Leu
            100                 105                 110

Val Thr Val Ser Ser
        115

<210> SEQ ID NO 29
<211> LENGTH: 106
<212> TYPE: PRT
<213> ORGANISM: Artificial sequence
<220> FEATURE:
<223> OTHER INFORMATION: Synthetic peptide
```

-continued

<400> SEQUENCE: 29

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Ala Pro Leu Thr
                85                  90                  95

Phe Gly Gly Gly Thr Lys Leu Glu Ile Lys
            100                 105

<210> SEQ ID NO 30
<211> LENGTH: 106
<212> TYPE: PRT
<213> ORGANISM: Artificial sequence
<220> FEATURE:
<223> OTHER INFORMATION: Synthetic peptide

<400> SEQUENCE: 30

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Ala Gly Gly Gly Thr Lys Leu Glu Ile Lys
            100                 105

<210> SEQ ID NO 31
<211> LENGTH: 117
<212> TYPE: PRT
<213> ORGANISM: Artificial sequence
<220> FEATURE:
<223> OTHER INFORMATION: Synthetic peptide

<400> SEQUENCE: 31

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

```
Leu Gln Ile Thr Ser Leu Thr Ala Glu Asp Thr Gly Met Tyr Phe Cys
                85                  90                  95

Val Arg Val Gly Tyr Asp Ala Leu Asp Tyr Ala Gly Gln Gly Thr Leu
            100                 105                 110

Val Thr Val Ser Ser
        115
```

VARIANTS OF HUMANIZED IMMUNOMODULATORY MONOCLONAL ANTIBODIES

This application claims the benefit of Application No. 61/511,055, filed Jul. 24, 2011.

FIELD OF THE INVENTION

The present invention relates to the field of immunotherapy and more specifically concerns humanized monoclonal antibodies useful for therapy of a variety of indications, particularly in the treatment of cancer and immunodeficiency disorders.

BACKGROUND OF THE INVENTION

The rapid increase of knowledge in recent years about the molecular and cellular bases of immune regulation, particularly at the level of T cell responses, provides a new arsenal of immunotherapeutic approaches including the development of anti-tumor vaccines. Certain monoclonal antibodies were shown to have immunomodulatory activity including the ability to bind determinants on the surface of T cells and to induce proliferation, activation, maturation or differentiation of these cells.

BAT (also referred to as mBAT-1 or BAT-1) is a murine monoclonal antibody generated against a membrane preparation of a Burkitt lymphoma cell line (Daudi) that was shown to exhibit antitumor and immunostimulatory effects towards various types of tumors (Hardy et al., 2001, Int. J. Oncol. 19:897). This monoclonal antibody was initially disclosed in U.S. Pat. No. 5,897,862 to Hardy et al. BAT-1 is secreted by the hybridoma cell line having CNCM Accession No. 1-1397. The immunomodulatory effect of murine BAT was studied also in vitro. Murine BAT activates CD4+ T cells and induces the secretion of IFN-γ from these cells (Hardy et al., 2000, Int. Immunol. 12:1623 and Quaglino E. et al., 2005, Vaccine 9:23(25):3280-7). In addition, it was found that BAT triggers the proliferation of T cells and increases their cytolytic activity (Hardy, B. et al., 1997, Hum. Antibodies, 8:95).

The polynucleotide and amino-acid sequences of murine BAT are disclosed in WO 00/58363, to Hardy et al., and U.S. Pat. No. 7,695,715.

A number of humanized monoclonal antibodies (mAbs) based on murine BAT are disclosed in U.S. Pat. No. 7,332,582, the contents of which are incorporated herein by reference. In particular embodiments of U.S. Pat. No. 7,332,582, the humanized monoclonal antibodies comprise a light chain variable region selected from SEQ ID NO: 1-4 (denoted BATRK$_D$, BATRK$_A$, BATRK$_B$ and BATRK$_C$, respectively) and a heavy chain variable region selected from SEQ ID NO: 5-9 (denoted BATRH$_C$, BATRH$_A$, BATRH$_B$, BATRH$_D$ and BATRH$_E$, respectively). The amino acid sequence of the light and heavy chain antibody variants are depicted in Table 1 herein below. The residues which differ in said variable regions are depicted with a gray background (positions 2, 30, 69, 77, 97 and 98 of the light region and positions 35, 69, 70 and 71 of the heavy chain).

According to U.S. Pat. No. 7,332,582, the humanized monoclonal BAT antibodies appear to induce a greater antitumor effect than those induced by the parent murine BAT antibody. Among various model systems tested, the BAT antitumor activity was studied in SCID (severe combined immunodeficiency disease) mice, beige mice that are deficient in NK cells and nude mice that are deficient in T cells (Hardy, B., 1997, Proc. Natl. Acad. Sci. USA 94:5756). All mice were injected intravenously with murine B16 melanoma cells that subsequently developed tumors in the lungs. BAT antibodies exerted an antitumor effect only in SCID mice that were engrafted with either murine or human lymphocytes. In the athymic nude mice and the beige mice BAT antibodies exerted an antitumor activity, though this activity was less effective as compared to the antitumor activity of BAT antibodies in the wild-type mice.

It should be borne in mind that BAT antibodies are not expected to target the tumor cells themselves but rather the immune-functioning cells of the subject or patient, in order to modulate the immune response in a beneficial way.

Berger et al. (2008) discloses administration of the humanized monoclonal antibody CT-011, which is based on mBAT-1, to patients with advanced hematologic malignancies, and associated pharmacokinetics (Berger et al. Clin. Cancer Res. 2008; 14(10) May 15, 2008).

WO 09/101,611 relates to methods for inhibiting tumor growth, increasing survival of a subject having a tumor and inducing protection against tumor recurrence in a mammal, comprising administering a humanized monoclonal antibody comprising CDR regions derived from the murine monoclonal antibody designated mBAT-1, in combination with at least one chemotherapeutic agent.

Nowhere in the background art is it taught or suggested that use of a humanized mBAT-1 monoclonal antibody comprising at least one site specific amino acid modification will be advantageous for the therapy of a variety of indications, particularly in the treatment of cancer and immuno-deficiency related diseases and disorders.

SUMMARY OF THE INVENTION

The present invention provides mutated humanized monoclonal antibodies or fragments thereof, having site specific amino acid modifications including but not limited to, amino acid substitutions and deletions, compared to the known humanized monoclonal antibodies hBAT-1. The invention further provides pharmaceutical compositions comprising the modified antibodies or fragments thereof, and use thereof for the treatment of cancer and immunodeficiency disorders. In some embodiments, the modified antibodies of the invention retain the immunomodulatory activity of hBAT-1, bind B lymphoblastoid cells and induce proliferation and activation of peripheral blood lymphocytes.

The antibodies of the present invention demonstrate superior features, e.g., enhanced bioactivity and stability and/or reduced immunogenicity, by virtue of a specific modification of at least one amino acid of the hBAT-1 antibody variants, as detailed herein below.

Table 1 lists the amino acid sequences of the variable and constant regions of the light and heavy chain of hBAT-1 antibody variants. The at least one amino acid which, in some embodiments, is substituted to produce the antibodies of the invention, is depicted in bold. In particular embodiments, the at least one amino acid is selected from the group consisting of: the amino acids in positions 5, 20, 71, 75, 76, 93 and 97 of SEQ ID NO: 1; the amino acids in positions 54, 55 and 107 of SEQ ID NO: 5, amino acids in positions 157, 158, 169, 170 of SEQ ID NO: 11; and the amino acids in positions 120, 124, 159, 160, 203, 204, 221, 222, 225, 252, 270, 271, 280, 281, 297, 298, 315, 316, 384, 385, 399, 400, 401, 402, 434, 435, 447 and 428 of SEQ ID NO: 13.

TABLE 1

The variable and constant region of the known hBAT-1 light and heavy chain

| Ig Chain | Region | Amino acid sequence | | SEQ ID NO: |
|---|---|---|---|---|
| Light Chain | Variable | EIVLTQSPSSLSASVGDRVTITCSARSSVS YMHWFQQKPGKAPKLWIYRTSNLASGVPSR FSGSGSGTSYCLTINSLQPEDFATYYCQQR SSFPLTFGGGTKLEIK | BATRK$_D$ | 1 |
| | Variable | EIVLTQSPSSLSASVGDRVTITCSARSSVS YMHWYQQKPGKAPKLWIYRTSNLASGVPSR FSGSGSGTDFTLTINSLQPEDFATYYCQQR SSFPLTFGGGTKLEIK | BATRK$_A$ | 2 |
| | Variable | EIVLTQSPSSLSASVGDRVTITCSARSSVS YMHWFQQKPGKAPKLWIYRTSNLASGVPSR FSGSGSGTDYTLTINSLQPEDFATYYCQQR SSFPLTFGGGTKLEIK | BATRK$_B$ | 3 |
| | Variable | EIVLTQSPSSLSASVGDRVTITCSARSSVS YMHWFQQKPGKAPKLWIYRTSNLASGVPSR FSGSGSGTDYCLTINSLQPEDFATYYCQQR SSFPLTFGGGTKLEIK | BATRK$_C$ | 4 |
| | Constant | RTVAAPSVFIFPPSDEQLKSGTASVVCLLN NFYPREAKVQWKVDNALQSGNSQESVTEQD SKDSTYSLSSTLTLSKADYEKHKVYACEVT HQGLSSPVTKSFNRGEC | | 10 |
| | Variable (BATRK$_D$) + Constant | EIVLTQSPSSLSASVGDRVTITCSARSSVS YMHWFQQKPGKAPKLWIYRTSNLASGVPSR FSGSGSGTSYCLTINSLQPEDFATYYCQQR SSFPLTFGGGTKLEIKRTVAAPSVFIFPPS DEQLKSGTASVVCLLNNFYPREAKVQWKVD NALQSGNSQESVTEQDSKDSTYSLSSTLTL SKADYEKHKVYACEVTHQGLSSPVTKSFNR GEC | | 11 |
| Heavy Chain | Variable | QVQLVQSGSELKKPGASVKISCKASGYTFT NYGMNWVRQAPGQGLQWMGWINTDSGESTY AEEFKGRFVFSLDTSVNTAYLQITSLTAED TGMYFCVRVGYDALDYWGQGTLVTVSS | BATRH$_C$ | 5 |
| | Variable | QVQLVQSGSELKKPGASVKISCKASGYTFS NYGMNWVRQAPGQGLQWMGWINTDSGESTY AEEFKGRFVFSLDTSVSTAYLQITSLTAED TGMYFCAKVGYDALDYWGQGTLVTVSS | BATRH$_A$ | 6 |
| | Variable | QVQLVQSGSELKKPGASVKISCKASGYTFT NYGMNWVRQAPGQGLQWMGWINTDSGESTY AEEFKGRFVFSLDTSVSTAYLQITSLTAED TGMYFCAKVGYDALDYWGQGTLVTVSS | BATRH$_B$ | 7 |
| | Variable | QIQLVQSGSELKKPGASVKISCKASGYTFT NYGMNWVRQAPGQGLQWMGWINTDSGESTY AEEFKGRFVFSLDTSVNTAYLQITSLTAED TGMYFCVRVGYDALDYWGQGTLVTVSS | BATRH$_D$ | 8 |
| | Variable | QIQLVQSGSELKKPGASVKISCKASGYTFT NYGMNWVRQAPGQGLQWMGWINTDSGESTY AEEFKGRFAFSLDTSVNTAYLQITSLTAED TGMYFCVRVGYDALDYWGQGTLVTVSS | BATRH$_E$ | 9 |
| | Constant | ASTKGPSVFPLAPSSKSTSGGTAALGCLVK DYFPEPVTVSWNSGALTSGVHTFPPAVLQSS GLYSLSSVVTVPSSSLGTQTYICNVNHKPS NTKVDKRVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | | 12 |

TABLE 1-continued

The variable and constant region of the known hBAT-1 light and heavy chain

| Ig Chain | Region | Amino acid sequence | SEQ ID NO: |
|---|---|---|---|
| | Variable (BATRH$_C$) + Constant | QVQLVQSGSELKKPGASVKISCKASGYTFT NYGMNWVRQAPGQGLQWMGWINTDSGESTY AEEFKGRFVFSLDTSVNTAYLQITSLTAED TGMYFCVRVGYDALDYWGQGTLVTVSSAST KGPSVFPLAPSSKSTSGGTAALGCLVKDYF PEPVTVSWNSGALTSGVHTFPAVLQSSGLY SLSSVVTVPSSSLGTQTYICNVNHKPSNTK VDKRVEPKSCDKTHTCPPCPAPELLGGPSV FLFPPKPKDTLMISRTPEVTCVVVDVSHED PEVKFNWYVDGVEVHNAKTKPREEQYNSTY RVVSVLTVLHQDWLNGKEYKCKVSNKALPA PIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK | 13 |

According to one aspect, the present invention provides an antibody or antigen binding fragment thereof comprising a light chain variable region selected from the group consisting of SEQ ID NO: 1, 2, 3, and 4, and a heavy chain variable region selected from the group consisting of SEQ ID NO: 5, 6, 7, 8, and 9, wherein the antibody or antigen binding fragment thereof comprises at least one amino acid substitution at a position selected from: Phe 97 and Phe 93 of the light chain variable region to Ala, Leu or Val, or a substitution of Trp 107 of the heavy chain variable region to Ala, Leu, Val or Tyr.

In some embodiments of the invention, the antibody or antigen binding fragment thereof comprises an amino acid substitution of Phe 97 of the light chain variable region and an amino acid substitution of Trp 107 of the heavy chain variable region. In another embodiment, the antibody or antigen binding fragment thereof comprises an amino acid substitution of Phe 93 of the light chain variable region and an amino acid substitution of Trp 107 of the heavy chain variable region.

In another embodiment, the light chain variable region comprises the amino acid sequence selected from the group consisting of: SEQ ID NO: 14, 15, 16, 17, 18, 19, 20 and 21. In one embodiment, the light chain variable region comprises the amino acid sequence as set forth in SEQ ID NO: 14. In another embodiment, the light chain variable region comprises the amino acid sequence as set forth in SEQ ID NO: 15. In a particular embodiment, the light chain variable region comprises the amino acid sequence as set forth in SEQ ID NO: 29. In yet another particular embodiment, the light chain variable region comprises the amino acid sequence as set forth in SEQ ID NO: 30.

In another embodiment, the heavy chain variable region comprises the amino acid sequence selected from the group consisting of: SEQ ID NO: 24, 25, 26, 27 and 28. In a particular embodiment, the heavy chain variable region comprises the amino acid sequence as set forth in SEQ ID NO: 24. In yet another particular embodiment, the heavy chain variable region comprises the amino acid sequence as set forth in SEQ ID NO: 31.

In yet another embodiment, the antibody or antigen binding fragment thereof further comprises at least one amino acid substitution at a position selected from the group consisting of: Thr 5, Thr 20, Cys 71, Asn 75, Ser 76 of the light chain variable region, and Asp 54 and Ser 55 of the heavy chain variable region.

According to another aspect, the present invention provides an antibody or antigen binding fragment thereof comprising a light chain variable region selected from the group consisting of SEQ ID NO: 1, 2, 3 and 4, and a heavy chain variable region selected from the group consisting of SEQ ID NO: 5, 6, 7, 8 and 9, wherein the antibody or antigen binding fragment thereof comprises at least one amino acid modification at a position selected from the group consisting of: Thr 5, Thr 20, Cys 71, Asn 75, Ser 76, Phe 93 and Phe 97 of the light chain variable region and Asp 54, Ser 55 and Trp 107 of the heavy chain variable region. Each possibility represents a separate embodiment of the present invention.

According to some embodiments of the invention, the amino acid modification is an amino acid substitution. According to one embodiment, the amino acid substitution is a conservative substitution. According to another embodiment, the amino acid substitution is a non-conservative substitution. According to another embodiment, the amino acid modification is an amino acid deletion. According to some embodiments, the modified antibodies of the invention comprise a combination of amino acid modifications, such as, an amino acid substitution of one residue and an amino acid deletion of another residue. According to another embodiment, the modified antibody comprises at least one amino acid substitution and at least one amino acid deletion.

According to various embodiments of the invention, the modified antibody or fragment thereof comprises a combination of a heavy chain variable region and a light chain variable region, the combination is selected from the group consisting of: SEQ ID NO: 5/SEQ ID NO: 1; SEQ ID NO: 6/SEQ ID NO: 2; SEQ ID NO: 7/SEQ ID NO: 2; SEQ ID NO: 7/SEQ ID NO: 3; SEQ ID NO: 8/SEQ ID NO: 3; and SEQ ID NO: 7/SEQ ID NO: 1. According to particular embodiments of the invention, the antibody or antigen binding fragment thereof comprises a combination of variable regions corresponding to SEQ ID NO: 5/SEQ ID NO: 1. The combination of the heavy and light chain variable region comprises, in one embodiment, at least one amino acid modification at a position selected from the group consisting of: Thr 5, Thr 20, Cys 71, Asn 75, Ser 76, Phe 93 and Phe 97 of the light chain variable region and Asp 54, Ser 55 and Trp 107 of the heavy chain variable region. In another embodiment, the combination of the heavy and light chain variable region comprises at least one amino acid modification at a position selected from: Phe 93 and Phe 97 of the light chain variable region and Trp 107 of the heavy chain variable region. Each possibility represents a separate embodiment of the present invention.

According to another embodiment of the invention, the antibody comprises a light chain constant region as set forth in SEQ ID NO: 10. According to yet another embodiment, the antibody comprises a modified light constant region comprising at least one amino acid modification at a position selected from the group consisting of: Asn 51, Ser 52, Asp 63 and Ser 64 of SEQ ID NO: 10. Each possibility represents a separate embodiment of the present invention.

According to another embodiment of the invention, the antibody comprises a light chain as set forth in SEQ ID NO: 11. According to yet another embodiment, the antibody comprises a modified light chain as set forth in SEQ ID NO: 11 comprising an amino acid modification at a position selected from the group consisting of: Asn 157, Ser 158, Asp 169 and Ser 170 of SEQ ID NO: 11. Each possibility represents a separate embodiment of the present invention.

According to another embodiment of the invention, the antibody comprises a heavy chain constant region as set forth in SEQ ID NO: 12. According to yet another embodiment, the antibody comprises a modified heavy chain constant region comprising at least one amino acid modification at a position selected from the group consisting of: Thr 3, Ser 7, Asn 42, Ser 43, Asn 86, His 87, Asp 104, Lys 105, Thr 108, Met 135, Asp 153, Pro 154, Asp 163, Gly 164, Asn 180, Ser 181, Asn 198, Gly 199, Asn 267, Gly 268, Asp 282, Ser 283, Asp 284, Ser 285, Asn 317, His 318, Lys 330 and Met 311 of SEQ ID NO: 12. Each possibility represents a separate embodiment of the present invention.

According to another embodiment of the invention, the antibody comprises a heavy chain as set forth in SEQ ID NO: 13. According to yet another embodiment, the antibody comprises a heavy chain as set forth in SEQ ID NO: 13 comprising at least one amino acid modification at a position selected from the group consisting of: Thr 120, Ser 124, Asn 159, Ser 160, Asn 203, His 204, Asp 221, Lys 222, Thr 225, Met 252, Asp 270, Pro 271, Asp 280, Gly 281, Asn 297, Ser 298, Asn 315, Gly 316, Asn 384, Gly 385, Asp 399, Ser 400, Asp 401, Ser 402, Asn 434, His 435, Lys 447 and Met 428 of SEQ ID NO: 13. Each possibility represents a separate embodiment of the present invention.

According to another aspect the present invention provides an antibody or antigen binding fragment thereof, the antibody comprises a light chain variable region selected from the group consisting of SEQ ID NO: 1, 2, 3 and 4 and or a heavy chain variable region selected from the group consisting of SEQ ID NO: 5, 6, 7, 8 and 9, or an amino acid sequence at least 85% identical thereto, wherein the antibody comprises at least one amino acid modification in a position selected from the group consisting of:

(i) Thr 5, Thr 20, Cys 71, Asn 75, Ser 76, Phe 93 and Phe 97 of the light chain variable region having the amino acid sequence of SEQ ID NO: 1-4;

(ii) Asp 54, Ser 55 and Trp 107 of the heavy chain variable region having the amino acid sequence of SEQ ID NO: 5-9;

(iii) Asn 51, Ser 52, Asp 63 and Ser 64 of the light chain constant region having the amino acid sequence of SEQ ID NO: 10; and (iv) Thr 3, Ser 7, Asn 42, Ser 43, Asn 86, His 87, Asp 104, Lys 105, Thr 108, Met 135, Asp 153, Pro 154, Asp 163, Gly 164, Asn 180, Ser 181, Asn 198, Gly 199, Asn 267, Gly 268, Asp 282, Ser 283, Asp 284, Ser 285, Asn 317, His 318, Lys 330 and Met 311 of the heavy chain constant region having the amino acid sequence of SEQ ID NO: 12.

In another embodiment of the invention, the antibody comprises a light chain variable region selected from the group consisting of SEQ ID NO: 1, 2, 3 and 4, or a heavy chain variable region selected from the group consisting of SEQ ID NO: 5, 6, 7, 8 and 9, or an amino acid sequence at least 88%, at least 90%, at least 92%, at least 93%, at least 94%, at least 95%, at least 96%, at least 97%, at least 98% or 99% identical thereto, wherein each possibility represents a separate embodiment of the present invention.

According to various embodiments of the invention, the antibody or antigen binding fragment thereof comprises a combination of modified amino acids, including but not limited to, at least two amino acid modifications, at least three amino acid modifications, at least four amino acid modifications or at least five amino acid modifications wherein each possibility represent a separate embodiment of the present invention.

According to another embodiment, the antibody or antigen binding fragment thereof comprises at least one amino acid modification at a position selected from the group consisting of: Thr 5, Thr 20, Cys 71, Asn 75, Ser 76, Phe 93 and Phe 97 of SEQ ID NO: 1-4; and at least one amino acid modification at a position selected from the group consisting of: Asp 54, Ser 55 and Trp 107 of SEQ ID NO: 5-9. Each possibility represents a separate embodiment of the present invention.

According to another embodiment, the light chain variable region has one amino acid modification selected from the group consisting of: Thr 5, Thr 20, Cys 71, Asn 75, Ser 76, Phe 93 and Phe 97 of any one of SEQ ID NO: 1, 2, 3, 4 or 11. According to yet another embodiment, the heavy chain variable region has one modified amino acid selected from the group consisting of: Asp 54, Ser 55 and Trp 107 of any one of SEQ ID NO: 5, 6, 7, 8, 9 or 13.

In a particular embodiment, the amino acid modification is at position Cys 71 of any one of SEQ ID NO: 1, 4 or 11. In another embodiment, Cys 71 is substituted with an amino acid selected from the group consisting of: Ser, Val, Gly, Thr, Ile, Leu and Ala. Without wishing to be bound by any theory or mechanism of action, the substitution of said Cystine residue reduces the risk of undesirable disulfide bonds.

Without wishing to be bound by any theory or mechanism of action, modifying one or both amino acid of the following amino acid pairs: Asn-Ser; Asp-Ser; Asn-His; or Asn-Gly, reduces the risk of deamidation thereby increasing the solubility of the antibody of the invention. In a specific embodiment, the amino acid modification is at a position selected from the group consisting of: Asn 75, Ser 76 of any one of SEQ ID NO: 1, 2, 3, 4 or 11. In another embodiment, the amino acid modification is at a position selected from the group consisting of: Asn 157, Ser 158 of SEQ ID NO: 10. In another embodiment, the amino acid modification is at a position selected from the group consisting of: Asn 159, Ser 160, Asn 297, Ser 298 of SEQ ID NO: 11.

In one embodiment, the amino acid pair Asn-Ser is a substituted with Ser-Asn. In another embodiment, the amino acid pair Asn-Ser is substituted with any amino acid pair other than Asp-Ser; Asn-His; or Asn-Gly. In particular embodiments, Asn is substituted with any amino acid selected from Ala, Val, Ser, Leu, Gly, Glu, or Ser. In another particular embodiment, Asn is substituted with any amino acid other than Gln or Asp. In particular embodiments, Ser is substituted with any amino acid selected from Ala, Val, Leu, Gly, Ile, Thr or Asn. In yet another particular embodiment, Ser is substituted with any amino acid selected from Ala, Val, Leu, Gly, Ile or Asn. In another particular embodiment, Ser is substituted with any amino acid other than Gly. Each possibility represents a separate embodiment of the present invention.

In another embodiment, the amino acid modification is at a position selected from the group consisting of: Asp 54, Ser 55 of any one of SEQ ID NO: 5, 6, 7, 8, 9 or 13.

In one embodiment, the amino acid pair Asp-Ser is a substituted with Ser-Asp. In another embodiment, the amino acid pair Asp-Ser is substituted with any amino acid pair other than Asn-Ser; Asn-His; or Asn-Gly. In particular embodiments, Asp is substituted with any amino acid selected from Ala, Val, Ser, Leu, Gly or Ser. In another particular embodiment, Asp is substituted with any amino acid other than Glu or Asn. In particular embodiments, Ser is substituted with any amino acid selected from Ala, Val, Leu, Ile, Gly or Asn. In another particular embodiment, Ser is substituted with any amino acid other than Gly. Each possibility represents a separate embodiment of the present invention.

In another embodiment, the modification is a substitution of at least one residue selected from the residue pairs: Asn 203 and His 204; Asn 315 and Gly 316; Asn 384 and Gly 385; Asn 434 and His 435 of SEQ ID NO: 11. In particular embodiments, the amino acid pair is interchanged (e.g., Asn-His substituted with His-Asn; Asn-Gly substituted with Gly-Asn). In another embodiment, the amino acid pair Asn-his is substituted with any amino acid pair other than Asn-Ser; Asp-Ser; or Asn-Gly. In another embodiment, the amino acid pair Asn-Gly is a substituted with any amino acid pair other than Asn-Ser; Asp-Ser; or Asn-His. Each possibility represents a separate embodiment of the present invention.

In another embodiment, the amino acid modification is at a position selected from Thr 5, Thr 20 of the light chain variable region. In another embodiment, the amino acid modification is at a position selected from the group consisting of: Thr 3, Ser 7 and Thr 108 of the heavy chain constant region as set forth as SEQ ID NO: 12. In yet another embodiment, the amino acid modification is at a position selected from the group consisting of: Thr 120, Ser 124, Thr 225 of the heavy chain as set forth as SEQ ID NO: 13. In another embodiment, the threonine residue is substituted with any amino acid other than serine. In another embodiment, the serine residue is substituted with any amino acid other than threonine. In a specific embodiment, the threonine and/or serine reside is substituted with an alanine reside. Without wishing to be bound by any theory or mechanism of action, the substitution of said threonine or serine residue reduces the risk of undesirable O-linked glycosylation.

Without wishing to be bound by any theory or mechanism of action, modifying one or both amino acid of the following amino acid pairs: Asp-Ser; Asp-Lys; Asp-Gly; reduces the risk of aspartic acid isomerization thereby preventing or decreasing the risk of degradation. In a specific embodiment, the amino acid modification is at a position selected from the group consisting of: Asp 63-Ser 64 of SEQ ID NO: 10; Asp 169-Ser 170 of SEQ ID NO: 11; Asp 104-Lys 105, Asp 163-Gly 164, Asp 282-Ser 283, Asp 285, Ser 286 of SEQ ID NO: 12; and Asp 221-Lys 222, Asp 280-Gly 281, Asp 339-Ser 400, Asp 401, Ser 402 of SEQ ID NO: 13. In particular embodiments, the amino acid pair is interchanged (e.g., Asp-Ser substituted with Ser-Asp). In another embodiment, the amino acid pair is substituted with any amino acid pair other than Asp-Ser, Asp-Lys or Asp-Gly. In one embodiment, Asp is substituted with Glu. Each possibility represents a separate embodiment of the present invention.

According to various embodiments, the antibody or antigen binding fragment thereof of the invention has an antitumor activity of similar, or greater than, mBAT-1. According to another embodiment, said antibody or antigen binding fragment thereof has an antitumor activity of similar, or greater than, hBAT-1. According to another embodiment, said antibody or antigen binding fragment thereof has enhanced stability as compared to hBAT-1.

According to various embodiments, the fragment of the humanized antibody is selected from the group consisting of: Fv, F(ab'), F(ab')2, and a single chain antibody.

According to another embodiment, the present invention provides polynucleotide sequences encoding the antibody of the invention or fragments thereof.

According to yet another embodiment there is provided a vector comprising the polynucleotide sequence encoding the antibody of the invention or fragments thereof. According to a specific embodiment there is provided a vector comprising the polynucleotide sequence encoding the antibody of the invention or fragments thereof selected from the group consisting of: whole humanized antibody, the light chain variable region, the heavy chain variable region, both chains of the variable region.

According to another aspect, there is provided host cells containing a vector comprising the polynucleotide sequence encoding the antibody of the invention or fragments thereof.

According to another aspect, there is provided a pharmaceutical composition comprising as an active ingredient the antibody of the invention or antigen binding fragment thereof, and a pharmaceutically acceptable carrier, diluent or stabilizer.

According to another embodiment, the pharmaceutical composition comprising as an active ingredient the antibody of the invention is used for the treatment of cancer. According to another embodiment, the pharmaceutical composition may be administered either following detection of primary or secondary tumors in a subject, or as preventive therapy of a subject having a high risk of developing cancers. According to some embodiments, the antibody of the invention elicits anti-tumor effects in a variety of tumors.

According to another aspect, the present invention provides a method for treating a disease or a disorder in a subject in need thereof, comprising administering to the subject an effective amount of a pharmaceutical composition comprising the antibody of the invention as an active ingredient or an antigen binding fragment thereof. In some embodiments, the disease or a disorder is cancer. In some embodiments, the disease or a disorder is an immunodeficiency related disease or disorder.

In one embodiment, the subject has a tumor selected from a solid tumor or a non-solid tumor. In some embodiments, the tumor is a solid tumor. In some embodiments, the tumor is a non-solid tumor. In some embodiments, the non-solid tumor is a hematologic malignancy.

In particular embodiments, the cancer is selected from the group consisting of a colorectal carcinoma, a non-small lung cancer (NSCLC), a small cell lung cancer (SCLC), a breast carcinoma; a melanoma; an ovarian carcinoma, a cervical carcinoma, a pancreatic cancer, a head and neck carcinoma, a gastrointestinal carcinoma, an esophageal tumor, a hepatocellular carcinoma, multiple myeloma, a renal cell carcinoma, a prostate tumor, non-Hodgkin's lymphoma, Hodgkin's disease, mantle cell lymphoma, Kaposi's sarcoma, a squamous cell carcinoma, a basal cell carcinoma, acute myeloid leukemia (AML), chronic myelocytic leukemia (CML), acute lymphocytic leukemia (ALL), and chronic lymphocytic leukemia (CLL). Each possibility represents a separate embodiment of the present invention.

According to specific embodiments, the cancer is selected from the group consisting of colorectal carcinoma, melanoma, pancreatic cancer, head and neck carcinoma, esophageal tumor, multiple myeloma, renal cell carcinoma, non-Hodgkin's lymphoma and Hodgkin's disease.

According to various embodiments, the subject is a non-human mammal. According to various preferred embodiments, the subject is a human.

In an additional aspect, the invention provides an antibody or antigen binding fragment thereof of the present invention, for use in treating a tumor. In another embodiment, the invention provides an antibody or antigen binding fragment thereof comprising a light chain variable region selected from the group consisting of SEQ ID NO: 1-4, and a heavy chain variable region selected from the group consisting of SEQ ID NO: 5-9, wherein the antibody or antigen binding fragment thereof comprises at least one amino acid modification at a position selected from the group consisting of: Thr 5, Thr 20, Cys 71, Asn 75, Ser 76, Phe 93 and Phe 97 of the light chain variable region and Asp 54, Ser 55 and Trp 107 of the heavy chain variable region, for use in treating a tumor.

In an additional aspect, the invention provides an antibody or antigen binding fragment thereof of the present invention, for the preparation of a medicament for treating a tumor. In another embodiment, the invention provides an antibody or antigen binding fragment thereof comprising a light chain variable region selected from the group consisting of SEQ ID NO: 1-4, and a heavy chain variable region selected from the group consisting of SEQ ID NO: 5-9, wherein the antibody or antigen binding fragment thereof comprises at least one amino acid modification at a position selected from the group consisting of: Thr 5, Thr 20, Cys 71, Asn 75, Ser 76, Phe 93 and Phe 97 of the light chain variable region and Asp 54, Ser 55 and Trp 107 of the heavy chain variable region, for the preparation of a medicament for treating a tumor.

Other features and advantages of the present invention will become apparent from the following detailed description and appended drawing figure.

BRIEF DESCRIPTION OF THE DRAWINGS

FIG. 1 is a graph demonstrating $CD4^+$ T lymphocytes viability following incubation with humanized monoclonal antibody BAT-1 (denoted CT-011) and a CT-011 double mutant comprising alanine substitutions at position Phe 97 of the light chain variable region and Trp 107 of the heavy chain variable region.

DETAILED DESCRIPTION OF THE INVENTION

The present invention provides humanized monoclonal antibodies, pharmaceutical compositions comprising said antibodies, and use thereof for the treatment of a variety of indications, including but not limited to cancer and immunodeficiency disorders. In particular, the present invention provides modified antibodies or fragments thereof having specific amino acid modifications such as, amino acid substitutions, compared to the hBAT-1 humanized monoclonal immunomodulatory antibody variants.

According to another embodiment, there is provided an antibody or antigen binding fragment thereof comprising a light chain variable region at least 85% identical to any one of SEQ ID NO: 1-4, and a heavy chain variable region at least 85% identical to any one of SEQ ID NO: 5-9, the antibody or antigen binding fragment thereof comprises at least one modified amino acid selected from the group consisting of: Thr 5, Thr 20, Cys 71, Asn 75, Ser 76, Phe 93 and Phe 97 in comparison with SEQ ID NO: 1, or at least one modified amino acid selected from the group consisting of: Asp 54, Ser 55 and Trp 107 in comparison with SEQ ID NO: 5. Each possibility represents a separate embodiment of the present invention.

In another embodiment of the invention, the antibody comprises a light chain variable region at least 85%, at least 90%, at least 92%, at least 95% or at least 98% identical to any one of SEQ ID NO: 1-4, and a heavy chain variable region as set forth in any one of SEQ ID NO: 5-9. In another embodiment, the antibody comprises a heavy chain variable region at least 85%, at least 90%, at least 92%, at least 95% or at least 98% identical to any one of SEQ ID NO: 5-9, and a light chain variable region as set forth in any one of SEQ ID NO: 1-4. In another embodiment, the antibody comprises a light chain variable region at least 85%, at least 90%, at least 92%, at least 95% or at least 98% identical to any one of SEQ ID NO: 1-4, and a heavy chain variable region at least 85%, at least 90%, at least 92%, at least 95% or at least 98% identical to any one of SEQ ID NO: 5-9. Each possibility represents a separate embodiment of the present invention.

The term "at least X percent identical" or "having at least X percent identity" refers to the percent of amino acid residues that are identical in the two compared sequences when the sequences are optimally aligned. Thus, for instance, 85% amino acid sequence identity means that 85% of the amino acids in two or more optimally aligned polypeptide sequences are identical.

According to another embodiment, there is provided an antibody or antigen binding fragment thereof comprising a light chain variable region selected from SEQ ID NO: 1-4, and a heavy chain variable region selected from SEQ ID NO: 5-9, wherein the light chain variable region comprises at least one amino acid modification at a position selected from the group consisting of: Thr 5, Thr 20, Cys 71, Asn 75, Ser 76, Phe 93 and Phe 97; or wherein the heavy chain variable region comprises at least one amino acid modification at a position selected from the group consisting of: Asp 54, Ser 55 and Trp 107. Each possibility represents a separate embodiment of the present invention.

According to one embodiment, the light chain variable region has the amino acid sequence as set forth in SEQ ID NO: 1 ($BATRK_D$). According to another embodiment, the light chain variable region has the amino acid sequence as set forth in SEQ ID NO: 2 ($BATRK_A$). According to another embodiment, the light chain variable region has the amino acid sequence as set forth in SEQ ID NO: 3 ($BATRK_B$). According to another embodiment, the light chain variable region has the amino acid sequence as set forth in SEQ ID NO: 4 ($BATRK_C$).

According to another embodiment, the antibody or a fragment thereof comprises at least one amino acid modification at a position selected from the group consisting of: Thr 5, Thr 20, Cys 71, Asn 75, Ser 76, Phe 93 and Phe 97 of any one of SEQ ID NO: 1 or SEQ ID NO: 4. Each possibility represents a separate embodiment of the present invention.

According to another embodiment, the antibody or a fragment thereof comprises at least one amino acid modification at a position selected from the group consisting of: Thr 5, Thr 20, Asn 75, Ser 76, Phe 93 and Phe 97 of any one of SEQ ID NO: 2 or SEQ ID NO: 3. Each possibility represents a separate embodiment of the present invention.

According to another embodiment, the heavy chain variable region has the amino acid sequence as set forth in SEQ ID NO: 5 ($BATRH_C$). According to another embodiment, the light chain variable region has the amino acid sequence as set forth in SEQ ID NO: 6 ($BATRH_A$). According to another embodiment, the light chain variable region has the amino acid sequence as set forth in SEQ ID NO: 7 ($BATRH_B$). According to another embodiment, the light chain variable region has the amino acid sequence as set forth in SEQ ID NO: 8 ($BATRH_D$). According to another embodiment, the light chain variable region has the amino acid sequence as set forth in SEQ ID NO: 9 (BATRH$_E$).

According to another embodiment, the antibody or antigen binding fragment thereof of the invention comprises an amino acid modification at a position selected from Phe 93 or Phe 97 of the light chain variable region. In another embodiment, the light chain variable region (any one of SEQ ID NO: 1-4) is modified by a substitution of Phe 93 or Phe 97 to any amino acid other than Trp and Tyr. Non limiting examples of amino acid substitutions of Phe and/or Trp include Ala, Leu and Val. In particular embodiments, the light chain variable region comprises the amino acid sequence selected from the group consisting of: SEQ ID NO: 14, 15, 16, 17, 18, 19, 20 and 21. In another particular embodiment, the light chain variable region comprises the amino acid sequence selected from the group consisting of: SEQ ID NO: 14, 16, 18, 20, and 22. In yet another particular embodiment, the light chain variable region comprises the amino acid sequence selected from the group consisting of: SEQ ID NO: 15, 17, 19, 21 and 23. In an additional embodiment, the light chain variable region comprises the amino acid sequence as set forth as SEQ ID NO: 14. In another embodiment, the light chain variable region comprises the amino acid sequence as set forth as SEQ ID NO: 15. In yet another embodiment, the Phe residue is substituted with an Ala residue.

In another embodiment, the light chain variable region comprises an amino acid substitution of Phe 93 and Phe 97 to Ala, Leu or Val. In a particular embodiment the light chain variable region comprises has the amino acid sequence of SEQ ID NO: 22. In yet another embodiment, the light chain variable region comprises an amino acid substitution of Phe 93 and Phe 97 to Ala. In a particular embodiment the light chain variable region comprises has the amino acid sequence of SEQ ID NO: 23.

In another embodiment of the invention, the heavy chain variable region (any one of SEQ ID NO: 5-9) is modified by a substitution of Trp 107 to any amino acid other than Phe. Non limiting examples of amino acid substitutions of Trp include Ala, Leu Tyr and Val. In particular embodiments, the heavy chain variable region comprises the amino acid sequence selected from the group consisting of: SEQ ID NO: 24, 25, 26, 27 and 28. In another embodiment, the heavy chain variable region comprises the amino acid sequence as set forth as SEQ ID NO: 24. In yet another embodiment, the Trp residue is substituted with an Ala residue.

According to another embodiment, the antibody or antigen binding fragment thereof comprises an amino acid modification at a position selected from Trp 107 of the heavy chain variable region and Phe 97 of the light chain variable region. According to yet another embodiment, the antibody or antigen binding fragment thereof comprises an amino acid modification of Trp 107 of the heavy chain variable region and Phe 97 of the light chain variable region. According to another embodiment, the antibody or antigen binding fragment thereof comprises an amino acid modification at a position selected from Trp 107 of the heavy chain variable region and Phe 93 of the light chain variable region. According to yet another embodiment, the antibody or antigen binding fragment thereof comprises an amino acid modification of Trp 107 of the heavy chain variable region and Phe 93 of the light chain variable region. In a specific embodiment, said modification is a substitution to an alanine residue.

TABLE 2

Exemplary variable region of hBAT-1 mutated light and heavy chain comprising F93, F97 or W107 amino acid substitutions.

| Ig Chain | Based on | Amino acid sequence | Substitution | SEQ ID NO: |
|---|---|---|---|---|
| Light chain variable region | BATRK$_D$ | EIVLTQSPSSLSASVGDRVTITCSARSSVS YMHWFQQKPGKAPKLWIYRTSNLASGVPSR FSGSGSGTSYCLTINSLQPEDFATYYCQQR SSXPLTFGGGTKLEIK | F93A, F93L or F93V | 14 |
| | BATRK$_D$ | EIVLTQSPSSLSASVGDRVTITCSARSSVS YMHWFQQKPGKAPKLWIYRTSNLASGVPSR FSGSGSGTSYCLTINSLQPEDFATYYCQQR SSFPLTXGGGTKLEIK | F97A, F97L or F97V | 15 |
| | BATRK$_A$ | EIVLTQSPSSLSASVGDRVTITCSARSSVS YMHWYQQKPGKAPKLWIYRTSNLASGVPSR FSGSGSGTDFTLTINSLQPEDFATYYCQQR SSXPLTFGGGTKLEIK | F93A, F93L or F93V | 16 |
| | BATRK$_A$ | EIVLTQSPSSLSASVGDRVTITCSARSSVS YMHWYQQKPGKAPKLWIYRTSNLASGVPSR FSGSGSGTDFTLTINSLQPEDFATYYCQQR SSFPLTXGGGTKLEIK | F97A, F97L or F97V | 17 |
| | BATRK$_B$ | EIVLTQSPSSLSASVGDRVTITCSARSSVS YMHWFQQKPGKAPKLWIYRTSNLASGVPSR FSGSGSGTDYTLTINSLQPEDFATYYCQQR SSXPLTFGGGTKLEIK | F93A, F93L or F93V | 18 |
| | BATRK$_B$ | EIVLTQSPSSLSASVGDRVTITCSARSSVS YMHWFQQKPGKAPKLWIYRTSNLASGVPSR FSGSGSGTDYTLTINSLQPEDFATYYCQQR SSFPLTXGGGTKLEIK | F97A, F97L or F97V | 19 |
| | BATRK$_C$ | EIVLTQSPSSLSASVGDRVTITCSARSSVS YMHWFQQKPGKAPKLWIYRTSNLASGVPSR FSGSGSGTDYCLTINSLQPEDFATYYCQQR SSXPLTFGGGTKLEIK | F93A, F93L or F93V | 20 |

TABLE 2-continued

Exemplary variable region of hBAT-1 mutated light and heavy chain comprising F93, F97 or W107 amino acid substitutions.

| Ig Chain | Based on | Amino acid sequence | Substitution | SEQ ID NO: |
|---|---|---|---|---|
| | BATRK$_C$ | EIVLTQSPSSLSASVGDRVTITCSARSSVS YMHWFQQKPGKAPKLWIYRTSNLASGVPSR FSGSGSGTDYCLTINSLQPEDFATYYCQQR SSFPLTXGGGTKLEIK | F97A, F97L or F97V | 21 |
| | BATRK$_D$ | EIVLTQSPSSLSASVGDRVTITCSARSSVS YMHWYQQKPGKAPKLWIYRTSNLASGVPSR FSGSGSGTDFTLTINSLQPEDFATYYCQQR SSXPLTXGGGTKLEIK | F93 & F97 to A, L or V | 22 |
| | BATRK$_D$ | EIVLTQSPSSLSASVGDRVTITCSARSSVS YMHWYQQKPGKAPKLWIYRTSNLASGVPSR FSGSGSGTDFTLTINSLQPEDFATYYCQQR SSAPLTAGGGTKLEIK | F93A & F97A | 23 |
| | BATRK$_D$ | EIVLTQSPSSLSASVGDRVTITCSARSSVS YMHWFQQKPGKAPKLWIYRTSNLASGVPSR FSGSGSGTSYCLTINSLQPEDFATYYCQQR SSAPLTFGGGTKLEIK | F93A | 29 |
| | BATRK$_D$ | EIVLTQSPSSLSASVGDRVTITCSARSSVS YMHWFQQKPGKAPKLWIYRTSNLASGVPSR FSGSGSGTSYCLTINSLQPEDFATYYCQQR SSFPLTAGGGTKLEIK | F97A | 30 |
| Heavy chain variable region | BATRH$_C$ | QVQLVQSGSELKKPGASVKISCKASGYTFT NYGMNWVRQAPGQGLQWMGWINTDSGESTY AEEFKGRFVFSLDTSVNTAYLQITSLTAED TGMYFCVRVGYDALDYXGQGTLVTVSS | W107A, W107L, W107Y or W107V | 24 |
| | BATRH$_A$ | QVQLVQSGSELKKPGASVKISCKASGYTFS NYGMNWVRQAPGQGLQWMGWINTDSGESTY AEEFKGRFVFSLDTSVSTAYLQITSLTAED TGMYFCAKVGYDALDYXGQGTLVTVSS | W107A, W107L, W107Y or W107V | 25 |
| | BATRH$_B$ | QVQLVQSGSELKKPGASVKISCKASGYTFT NYGMNWVRQAPGQGLQWMGWINTDSGESTY AEEFKGRFVFSLDTSVSTAYLQITSLTAED TGMYFCAKVGYDALDYXGQGTLVTVSS | W107A, W107L, W107Y or W107V | 26 |
| | BATRH$_D$ | QIQLVQSGSELKKPGASVKISCKASGYTFT NYGMNWVRQAPGQGLQWMGWINTDSGESTY AEEFKGRFVFSLDTSVNTAYLQITSLTAED TGMYFCVRVGYDALDYXGQGTLVTVSS | W107A, W107L, W107Y or W107V | 27 |
| | BATRH$_E$ | QIQLVQSGSELKKPGASVKISCKASGYTFT NYGMNWVRQAPGQGLQWMGWINTDSGESTY AEEFKGRFAFSLDTSVNTAYLQITSLTAED TGMYFCVRVGYDALDYXGQGTLVTVSS | W107A, W107L, W107Y or W107V | 28 |
| | BATRH$_C$ | QVQLVQSGSELKKPGASVKISCKASGYTFT NYGMNWVRQAPGQGLQWMGWINTDSGESTY AEEFKGRFVFSLDTSVNTAYLQITSLTAED TGMYFCVRVGYDALDYAGQGTLVTVSS | W107A | 31 |

According to another embodiment, the present invention provides polynucleotide sequences encoding the antibody of the invention or fragments thereof. Accordingly, the modified antibody is produced by expression of polynucleotides, wherein the polynucleotides may encode the whole humanized antibody or the light chain variable region or the heavy chain variable region or the variable region of both chains of the humanized antibody. Further, the humanized antibody may be expressed in a host cell following co-transfection of distinct vectors each comprising polynucleotides encoding the heavy or the light chain, or by transfection of a single vector comprising both light and heavy chain polynucleotide sequences.

According to yet another embodiment there is provided a vector comprising the polynucleotide sequence encoding the modified antibody of the invention or fragments thereof.

According to yet another embodiment there is provided a vector comprising the polynucleotide sequence encoding the modified antibody of the invention or fragments thereof selected from the group consisting of: whole humanized antibody, the light chain variable region, the heavy chain variable region, both chains of the variable region.

According to yet another embodiment, the vector further comprises at least one sequence encoding a component selected from the group consisting of: resistance genes, promoter, signal peptide, polyA transcription terminator, selection markers, genomic human kappa constant region.

According to yet another preferred embodiment, the components of the vector are selected from the group consisting of: Ampicillin resistance gene, Neomycin resistance gene, HCMV Immediate Early Promoter, the genomic human kappa constant region, a mouse immunoglobulin signal peptide sequence, Kozak sequence, a signal sequence intron, BGH polyA transcription terminator, a Neo/G418 selection marker, a hamster dhfr selection marker.

According to yet another embodiment, the vector further comprises at least one sequence encoding a component selected from the group consisting of: resistance genes, promoter, signal peptide, polyA transcription terminator, selection markers, the genomic human Ig constant region.

According to yet another preferred embodiment, the components of the vector are selected from the group consisting of: Ampicillin resistance gene, Neomycin resistance gene, HCMV Immediate Early Promoter, the genomic human IgG1 constant region, a mouse immunoglobulin signal peptide sequence, Kozak sequence, a signal sequence intron, BGH polyA transcription terminator, a Neo/G418 selection marker, a hamster dhfr selection marker.

According to another aspect, there is provided host cells containing a vector comprising the polynucleotide sequence encoding the antibody of the invention or fragments thereof for the purposes of storage, propagation, antibody production and therapeutic applications.

According to another embodiment, the host cell may be selected from the group consisting of: CHO, CHOdhfr, NSO, NSO/GS, COS, COST.

Definitions

The term "modified antibodies", "mutated antibodies" and similar grammatical expressions refer to an alteration in an amino acid sequence, for example by substitution or deletion or chemical modification of one or more amino acid residues, as compared to the sequence of the original, known humanized monoclonal antibodies BAT-1 immunoglobulin.

The "humanized monoclonal antibodies hBAT-1" relates to a number of humanized monoclonal antibodies, based on murine BAT (mBAT-1), disclosed in U.S. Pat. No. 7,332,582 (the contents of which are incorporated herein by reference). The hBAT-1 mAbs comprise a light chain variable region selected from the group consisting of: SEQ ID NO: 1, 2, 3 and 4 (denoted BATRK$_D$, BATRK$_A$, BATRK$_B$ and BATRK$_C$, respectively) and a heavy chain variable region selected from the group consisting of: SEQ ID NO: 5, 6, 7, 8 and 9 (denoted BATRH$_C$, BATRH$_A$, BATRH$_B$, BATRH$_D$ and BATRH$_E$, respectively). The amino acid sequence of the light and heavy chain antibody variants (SEQ ID NO: 1, 2, 3, 4, 5, 6, 7, 8 and 9) are depicted in Table 1. The residues which differ in said variable regions are depicted with a gray background (positions 2, 30, 69, 77, 97 and 98 of the light region and positions 35, 69, 70 and 71 of the heavy chain). The polynucleotide and amino-acid sequences of murine BAT (mBAT-1) are disclosed in U.S. Pat. No. 7,695,715, the contents of which are incorporated herein by reference. Particular combinations of a heavy chain variable region and a light chain variable region of the hBAT-1 antibody are selected from the group consisting of: SEQ ID NO: 5/SEQ ID NO: 1; SEQ ID NO: 6/SEQ ID NO: 2; SEQ ID NO: 7/SEQ ID NO: 2; SEQ ID NO: 7/SEQ ID NO: 3; SEQ ID NO: 8/SEQ ID NO: 3; and SEQ ID NO: 7/SEQ ID NO: 1. In specific embodiment of the present invention, the mutated antibodies are based on the above particular combinations of heavy and light chain variable regions and comprise at least one site specific modification such as substitution selected from the disclosed amino acids.

An "amino acid modification" as used herein refers to an alteration in the amino acid, for example by substitution or deletion or chemical modification of said amino acid. Further, the antibodies of the invention may be chemically modified at one or more amino acid residues, either by natural processes, such as processing or other post-translational modifications, or by chemical modification techniques. Chemical modifications include, without limitation, acetylation, acylation, amidation, ADP-ribosylation, glycosylation, GPI anchor formation, covalent attachment of a liquid or lipid derivative, methylation, myristylation, pegylation, prenylation, phosphorylation, ubiquitnation, or any similar process.

The term "amino acid" is used in its broadest sense to include naturally occurring amino acids as well as non-naturally occurring amino acids including amino acid analogs. In view of this broad definition, one skilled in the art would know that reference herein to an amino acid includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway. The amino acids used in this invention are those which are available commercially or are available by routine synthetic methods. Certain residues may require special methods for incorporation into the peptide, and either sequential, divergent and convergent synthetic approaches to the peptide sequence are useful in this invention. When there is no indication, either the L or D isomers may be used.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (Ala; A), Serine (Ser; S), Threonine (Thr; T);
2) Aspartic acid (Asp; D), Glutamic acid (Glu; E);
3) Asparagine (Asn; N), Glutamine (Gln; Q);
4) Arginine (Arg; R), Histidine (His, H), Lysine (Lys; K);
5) Isoleucine (Ile; I), Leucine (Leu; L), methionine (Met; M), Valine (Val; V); and
6) Phenylalanine (Phe; F), Tyrosine (Tyr; Y), Tryptophan (Trp; W).

According to one embodiment, the amino acid substitution is a conservative substitution.

According to another embodiment, the amino acid substitution is a non-conservative substitution. As used herein, a "non-conservative substitution" is any amino acid substitution other than a conservative substitution described above. Non limiting examples for non-conservative substitutions include substitution of phenylalanine or tryptophan to alanine, leucine or valine.

In a specific embodiment the amino acid modification substitutions of the invention (i.e., to produce the modified antibody of the invention) is other that the substitutions described in U.S. Pat. No. 7,332,582.

The term "antibody" (also referred to as an "immunoglobulin") is used in the broadest sense and specifically encompasses monoclonal antibodies (including full length monoclonal antibodies) and antibody fragments so long as they exhibit the desired biological activity. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments.

The basic unit of the naturally occurring antibody structure is a heterotetrameric glycoprotein complex of about 150,000 daltons, composed of two identical light (L) chains and two identical heavy (H) chains, linked together by both noncovalent associations and by disulfide bonds. Each heavy and light chain also has regularly spaced intrachain disulfide bridges. Five human antibody classes (IgG, IgA, IgM, IgD and IgE) exist, and within these classes, various subclasses, are recognized on the basis of structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody which are other than the hypervariable region amino acid residues as herein defined. The term "hypervariable region" as used herein refers to the amino acid residues in the variable domain of an antibody which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al., ibid).

The term "acceptor human immunoglobulin" refers to the human immunoglobulin providing the framework for a humanized antibody.

As used herein, the term "humanized antibody" refers to an antibody comprising a framework region from a human antibody and one or more CDRs from a non-human (usually a mouse or rat) immunoglobulin. Parts of a humanized immunoglobulin, except possibly the CDRs, are substantially identical to corresponding parts of natural human immunoglobulin sequences. In some cases however, specific amino acid residues, for example in the framework regions, may be modified, so as to optimize performance of the humanized antibody. Importantly, the humanized antibody is expected to bind to the same antigen as the donor antibody that provides the CDRs. For further details, see e.g. U.S. Pat. No. 5,225,539 assigned to Medical Research Council, UK.

The terms "a framework region from an acceptor human immunoblobulin" and "a framework region derived from an acceptor human immunoblobulin", and similar grammatical expressions are used interchangeably herein to refer to a framework region or portion thereof that has the same amino acid sequence of the acceptor human immunoblobulin.

The term "human antibody" refers to an antibody encoded by a gene actually occurring in a human, or an allele, variant or mutant thereof.

The modified humanized monoclonal antibody of the invention is preferably generated by recombinant DNA technology, utilizing CDR grafting.

The term "mammal" means any mammal, including pet animals, such as dogs and cats; farm animals, such as pigs, cattle, sheep, and goats; laboratory animals, such as mice and rats; primates, such as monkeys, apes, and chimpanzees; and preferably, humans.

Methods of the Invention

Cancer immunotherapeutics are aimed by and large at modulating the response of the immune system to induce or enhance killing of tumor cells and control tumor growth. This approach utilizes using various immunomodulators including monoclonal antibodies that selectively bind to specific determinants on T cells thereby either initiating an activation pathway or inducing an inhibitory effect.

According to another aspect, the present invention provides a method for diagnosis or treatment of a disease or a disorder, particularly cancer, comprising administering to a subject in need thereof, an effective amount of a pharmaceutical composition comprising the antibody of the invention or a fragment thereof as an active ingredient.

All types of tumors may be treated by the methods of the present invention. The tumors may be solid or non-solid.

Some examples of solid tumors that can be treated with the combination of the present invention include carcinomas, sarcomas, blastomas or gliomas. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, liver tumors, esophageal tumors and gastric tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers include squamous cell carcinoma, basal cell carcinoma and skin cancers that can be treated by suppressing the growth of malignant keratinocytes, such as human malignant keratinocytes.

Some examples of non-solid tumors include leukemias, multiple myelomas and lymphomas. Some examples of leukemias include acute myelocytic leukemia (AML), chronic myelocytic leukemia (CML), acute lymphocytic leukemia (ALL), chronic lymphocytic leukemia (CLL), erythrocytic leukemia or monocytic leukemia. Some examples of lymphomas include lymphomas associated with Hodgkin's disease, Non-Hodgkin's disease or mantle cell lymphoma.

Currently preferred types of tumors are selected from the following group: colorectal carcinoma; lung carcinoma including non-small lung cancer (NSCLC) and small cell lung cancer (SCLC); breast carcinoma; melanoma; ovarian carcinoma; cervical carcinoma, pancreatic cancer; head and neck carcinoma; gastrointestinal carcinoma; esophageal tumors; hepatocellular carcinoma; multiple myeloma; renal cell carcinoma; prostate tumors; non-Hodgkin's lymphoma; Hodgkin's disease; mantle cell lymphoma; Kaposi's sarcoma; squamous cell carcinoma; basal cell carcinoma; acute myeloid leukemia (AML); chronic myelocytic leukemia (CML); acute lymphocytic leukemia (ALL); chronic lymphocytic leukemia (CLL).

The term "antitumor effect" as used herein, refers to a beneficial biological effect, which can be manifested by any one or more of: a decrease or stabilization of tumor volume, a decrease or stabilization of the number of tumor cells, a decrease or stabilization of the rate of tumor growth, a decrease or stabilization of the number of metastases, protection from tumor recurrence, an increase in life expectancy or survival of the subject with the tumor, an increase in life expectancy or survival without disease progression of the subject with the tumor or amelioration of various physiological symptoms associated with the cancerous condition. An "antitumor effect" can also be manifested by the ability to prevent the occurrence of tumor in the first place or the recurrence of the tumor. Given its properties, the methods of the invention can be used in the treatment of acute cancer, of dormant, controlled or stabilized cancer, as well as in cancer prophylaxis.

The term "enhanced survival", as used herein, refers to a prolonged length of time during which the subject or patient is alive following treatment with a method of the invention. Enhanced survival denotes the increased probability of staying free of disease progression for an individual suffering from cancer after a particular treatment. It is also used to describe the elevated percentage of individuals in a group whose disease is likely to remain stable (not showing signs of progression) after a specified duration of time, compared to a control group. It is also used to describe the elevated percentage of individuals in a group whose disease is likely to be cured (not showing signs of disease) after a specified duration of time, compared to a control group. This parameter may be measured by any one of the customary clinical endpoints denoted as "progression-free survival", "overall survival" and "disease free survival" used as an indication of the efficacy of a particular treatment.

The term "tumor recurrence" refers to the re-emergence, reappearance, re-growth or proliferation of a tumor of the same type in either the same location or a different location, following a period during which the growth of the original tumor has been reversed, arrested or inhibited.

The term "enhances or increases lymphocyte survival" as used herein refers to the ability of the antibodies of the invention to prolong the viability of lymphocytes in vitro or in vivo, as compared to the viability of an identical cell population not contacted with the antibody of the invention. With regard to the combination therapy of the invention, the term refers to the ability of a particular combination of treatments to prolong the viability of lymphocytes in vitro or in vivo, as compared to the viability of an identical cell population with only one of the treatments.

An antitumor activity of similar to mBAT-1 or hBAT-1 refers to an antitumor effect of about 5%, or not more than 10%, similar to the antitumor effect of mBAT-1 or hBAT-1. An antitumor activity of greater than mBAT-1 or hBAT-1 refers to an antitumor activity of more than 10%, more than 30% or more than 30%, as compared to the antitumor activity of greater than mBAT-1 or hBAT-1.

According to another embodiment, the antibody of the invention in administered together with, prior to, or following, the administration of other agents, which can act in an additive or synergistic manner with it.

According to yet another embodiment, the antibody of the invention in administered together with, prior to, or following, the administration of agents selected from the group consisting of: cytokines, IL-1 (Interleukin-1), IL-2, IL-6, IFN-α (Interferon-α), cell vaccines, antibodies, T-cell stimulatory antibodies, anti-tumor therapeutic antibodies. Each possibility is a separate embodiment of the present invention.

In another embodiment, the disease or a disorder treated by the methods of the invention is an immuno-deficiency related disease or disorder selected from severe combined immunodeficiency disease, acquired immunodeficiency syndrome, and any disorder that involves depletion, attenuation and/or malfunctioning of lymphocytes, specifically T cells, NK cells, NK-T cells, B cells, monocytes, macrophages or any combination thereof.

In another embodiment, the disease or a disorder is an immunodeficiency, immune malfunction or immune incompetence, collectively referred to hereinafter as immunodeficiency disorders, established after chemotherapy or irradiation. According to certain embodiments, the pharmaceutical composition comprising the antibody of the invention is used in conjunction with autologous, allogeneic or syngeneic stem cell transplantation derived from the bone marrow, umbilical cord blood or peripheral blood and donor leukocyte infusion.

According to yet another embodiment, the immunodeficiency disorder is selected from the group consisting of: severe combined immunodeficiency disease, acquired immunodeficiency syndrome, X-linked agammaglobulinaemia, common variable immunodeficiency, IgA deficiency, IgG subclass deficiency, Wiskott-Aldrich syndrome, DiGeorge anomaly, Ataxia Telangiectasia, adenosine deaminase deficiency and activation-induced cytidine deaminase deficiency.

According to yet another embodiment, the immunodeficiency disorder is related to viral infection, fungal infection or bacterial infection. According to yet another embodiment, the immunodeficiency disorder is associated with intoxication.

According to yet another embodiment, the method of the invention is used for treating anemia, particularly, aplastic anemia and myelodysplastic syndromes (MDS), primarily for avoiding further complication of the anemia due to immunodeficiency disorders.

Combination Therapy with Chemotherapy

According to certain aspects of the present invention, administration of the immunostimulatory humanized antibody comprising modified amino acids in conjunction with at least one antitumor chemotherapeutic agent acts to enhance the antitumor effect of chemotherapeutic agents, and vice versa. In preferred embodiments, the combinations of the immunostimulatory antibody together with the at least one chemotherapeutic agent improve the clinical outcome in a significant manner versus each of the treatments alone. In a preferred embodiment, there is synergy when tumors are treated with the humanized antibody of the invention in conjunction with at least one chemotherapeutic agent, and, optionally further in conjunction with radiation.

In other words, according to one aspect of the present invention the antitumor effect of the humanized antibody of the invention is augmented more than expected when combined with at least one chemotherapeutic agent.

Antitumor effect induced by the combinations of the invention includes the prevention, inhibition of the progression of a tumor, reduction of tumor growth and protection against tumor recurrence, including cancerous and noncancerous tumors. The progression of a tumor includes the invasiveness, metastasis, recurrence and increase in size of the tumor. The reduction of tumor growth also includes the destruction or elimination of a tumor leading to complete remission.

In another embodiment, the antibody of the invention is effective for improving tolerability to chemotherapeutic agents. As is known in the art, a major setback for patients undergoing cancer chemotherapy is the appearance of severe and detrimental adverse side effects due to the potent toxicity of most chemotherapeutic agents.

The invention further provides a method of enhancing survival in a subject with a tumor, which comprises administration of the humanized antibody of the invention, either on its own, or optionally, combined with the further administration of one or more chemotherapeutic agents.

The invention further provides a method of reducing or preventing recurrence of a tumor, which comprises administration of the humanized antibody of the invention, either on its own, or optionally, combined with the further administration of one or more chemotherapeutic agents. In some embodiments, combination treatment of experimental animals using the humanized antibody of the invention and chemotherapeutic agents induced a "memory" effect, such that tumor recurrence is inhibited upon re-challenge with the original tumor type.

According to another embodiment, the present invention provides a method of treating a tumor, the method comprising (i) administering to a subject in need thereof an effective amount of an antibody of the invention or a fragment thereof; and (ii) administering to the subject an effective amount of at least one chemotherapeutic agent; thereby treating the tumor.

According to another embodiment, the invention further provides a method of improving tolerability to at least one chemotherapeutic agent, the method comprising administering to a subject in need thereof an effective amount of an antibody of the invention or a fragment thereof, wherein the subject is undergoing chemotherapy with at least one chemotherapeutic agent; thereby improving tolerability to said chemotherapeutic agent.

The term "tolerability to chemotherapeutic agents" refers to the physiological, physicochemical and immunological capacity of a subject to tolerate the adverse side effects associated with treatment with one or more chemotherapeutic agents. Accordingly, the term "improving tolerability to chemotherapeutic agents" refers to increasing the physiological and physicochemical capacity to such adverse side effects, such that the severity of the adverse side effects is decreased and/or the number of side effects is decreased. Accordingly, "improving tolerability to chemotherapeutic agents" may refer to improving the quality of life of cancer patients treated with chemotherapeutic agents.

According to yet another embodiment of the invention there is provided a method of enhancing survival or inhibiting disease progression in a subject having a tumor, wherein the subject is treated with at least one chemotherapeutic agent, the method comprising administering an effective amount of an antibody of the invention or a fragment thereof, thereby enhancing survival of the subject.

According to yet another embodiment, the invention provides a method of reducing or preventing tumor recurrence, the method comprising administering to a subject in need thereof an effective amount of an antibody of the invention or a fragment thereof, thereby reducing or preventing tumor recurrence. According to one embodiment, the method of reducing or preventing tumor recurrence further comprises administering to the subject at least one chemotherapeutic agent. According to particular embodiments, the subject is undergoing or has completed a course of chemotherapy with at least one chemotherapeutic agent.

According to various embodiments, the administering of the antibody of the invention and of the at least one chemotherapeutic agent is carried out substantially simultaneously, concurrently, alternately, sequentially or successively. In some embodiments, the antibody and the at least one chemotherapeutic agent are administered according to overlapping schedules.

According to particular embodiments, administering of the antibody is carried out prior to initial administration of the at least one chemotherapeutic agent.

According to other embodiments, administering of either or both of the antibody and the at least one chemotherapeutic agent is carried out by a route selected from the group consisting of intravenous, oral, intraperitoneal, subcutaneous, isolated limb perfusion, infusion into an organ and combinations thereof.

In particular embodiments, the methods of the invention further comprise assessing at least one parameter selected from the group consisting of: rate of tumor growth, tumor volume, number of metastases, tumor recurrence and combinations thereof.

It should be noted that according to the teaching of the present invention, the modified humanized antibody of the invention may be administered before, during, or after commencing chemotherapy and, optionally, radiation therapy, as well as any combination thereof, i.e. before and during, before and after, during and after, or before, during, and after commencing the chemotherapy and, optionally, the radiation therapy. For example, the antibody of the invention may be administered between 1 and 30 days prior to or after commencing chemotherapy. The antibody may further be administered between courses of chemotherapy.

In the combination therapy methods of the invention, the antibodies may be administered in parallel to the chemotherapy, for example substantially simultaneously or concurrently. Other administration schedules may also be used, for example, overlapping schedules or those which involve alternately, sequentially or successively administering the two types of treatment.

According to various embodiments, the at least one chemotherapeutic agent is selected from the group consisting of: antimetabolites, platinum-based drugs, mitotic inhibitors, anthracycline antibiotics, topoisomerase inhibitors, anti-angiogenic agents and combinations thereof.

According to another particular embodiment, the at least one chemotherapeutic agent is selected so that the modified hBAT-1 of the invention enhances survival of lymphocytes when used in combination with the chemotherapeutic agent. Typically, the enhanced or increased survival may be conveniently assayed in vitro.

Accordingly, in various embodiments, the chemotherapeutic agent may be selected from an antimetabolite, such as the pyrimidine analog 5-fluorouracil, or cytarabin, or a platinum-based drug, such as oxaliplatin or cisplatin. Further, in various embodiments, the chemotherapeutic agent may be other than an agent selected from a topoisomerase I inhibitor (such as SN-38) and an alkylating agent (such as cyclophosphamide).

According to some embodiments, the at least one chemotherapeutic agent is an antimetabolite, including purine antagonists, pyrimidine antagonists and folate antagonists. According to some embodiments, the antimetabolite is a pyrimidine antagonist. According to some embodiments, the antimetabolite is selected from the group consisting of: 5-fluorouracil, uracil mustard, uracil, capecitabine, 6-mercaptopurine, methotrexate, gemcitabine, cytarabine, fludarabine, and pemetrexed.

According to some embodiments, the at least one chemotherapeutic agent is 5-fluorouracil. According to some embodiments, the at least one chemotherapeutic agent is cytarabine. According to some embodiments, the at least one chemotherapeutic agent is a platinum-based drug selected from the group consisting of: cisplatin, carboplatin and oxaliplatin. According to yet other embodiments, the at least one chemotherapeutic agent is a mitotic inhibitor selected from the group consisting of: paclitaxel, docetaxel, etoposide, vinblastine, vincristine and vinorelbine. According to yet other embodiments, the at least one chemotherapeutic agent is an anthracycline antibiotic selected from the group consisting of: daunorubicin, respinomycin D and idarubicin. According to some embodiments, the at least one chemotherapeutic agent is an anti-angiogenic agent selected from the group consisting of: bevacizumab, dopamine, tetrathiomolybdate, and antiangiogenic variants of VEGF. According to some embodiments, the at least one chemotherapeutic agent is other than a topoisomerase I inhibitor. According to some embodiments, the at least one chemotherapeutic agent is other than an alkylating agent.

Chemotherapy drugs are divided into several groups based on their effect on cancer cells, the cellular activities or processes the drug interferes with, or the specific phases of the cell cycle the drug affects. Accordingly, chemotherapy drugs fall in one of the following categories: alkylating agents, nitrosoureas, antimetabolites, anthracyclines, topoisomerase I and II inhibitors, mitotic inhibitors, inter alia platinum based drugs, steroids and antiangiogenic agents.

Antimetabolites, also termed "nucleoside analogs", replace natural substances as building blocks in DNA molecules, thereby altering the function of enzymes required for cell metabolism and protein synthesis. In the event that they mimic nutrients required for cell growth, the cells eventually undergo lysis. If a nucleoside is replaced with a nonfunctional nucleoside analog, the latter is incorporated into DNA and RNA, finally inducing cell cycle arrest and apoptosis by inhibiting the cell's ability to synthesize DNA. Antimetabolites are cell-cycle specific and are most effective during the S-phase of cell division as they primarily act upon cells undergoing synthesis of new DNA for formation of new cells. The toxicities associated with these drugs are seen in cells that are growing and dividing quickly. Examples of antimetabolites include purine antagonists, pyrimidine antagonists, and folate antagonists. These agents damage cells during the S phase and are commonly used to treat leukemias, tumors of the breast, ovary, and the gastrointestinal tract, as well as other cancers. Specific examples of antimetabolites include 5-fluorouracil (also known as 5FU), capecitabine, 6-mercaptopurine, methotrexate, gemcitabine, cytarabine, fludarabine and pemetrexed.

Platinum-based chemotherapeutic drugs crosslink DNA in several different ways, interfering with cell division by mitosis. The damaged DNA elicits DNA repair mechanisms, which in turn activate apoptosis when repair proves impossible. Most notable among the DNA changes are the 1,2-intrastrand cross-links with purine bases. These include 1,2-intrastrand d(GpG) adducts which form nearly 90% of the adducts and the less common 1,2-intrastrand d(ApG) adducts. 1,3-intrastrand d(GpXpG) adducts occur but are readily excised by the nucleotide excision repair (NER). Other adducts include inter-strand crosslinks and nonfunctional adducts that have been postulated to contribute to the activity of platinum-based drugs. Interaction with cellular proteins, particularly HMG domain proteins, has also been advanced as a mechanism of interfering with mitosis, although this is probably not its primary method of action. Platinum-based chemotherapeutic drugs include cisplatin (also known as cisplatinum or cis-diamminedichloridoplatinum II (CDDP), carboplatin and oxaliplatin. Cisplatin is frequently designated as an alkylating agent, though it has no alkyl group and cannot carry out alkylating reactions. It is correctly classified as alkylating-like. Platinum-based chemotherapeutic drugs are used to treat various types of cancers, including sarcomas, some carcinomas (e.g. small cell lung cancer, and ovarian cancer), lymphomas and germ cell tumors.

Mitotic inhibitors interfere with cell division. The most known chemotherapeutic agent in this category is paclitaxel (also known as Taxol®, "plant alkaloid", "taxane" and an "antimicrotubule agent"). Together with docetaxel, it forms the drug category of the taxanes. However, other mitotic inhibitors are known, including, but not limited to etoposide, vinblastine and vincristine. Paclitaxel acts by interfering with normal microtubule growth during cell division by arrests their function; it hyper-stabilizes their structure. This destroys the cell's ability to use its cytoskeleton in a flexible manner. Specifically, paclitaxel binds to the β subunit of tubulin, the "building block" of microtubules, and the binding of paclitaxel locks these building blocks in place. The resulting microtubule/paclitaxel complex does not have the ability to disassemble. This adversely affects cell function because the shortening and lengthening of microtubules (termed dynamic instability) is necessary for their function as a mechanism to transport other cellular components. For example, during mitosis, microtubules position the chromosomes all through their replication and subsequent separation into the two daughter-cell nuclei. Furthermore, paclitaxel induces programmed cell death (apoptosis) in cancer cells by binding to the apoptosis stopping protein Bcl-2 (B-cell leukemia 2) and thus arresting its function.

Another group of DNA-interacting drugs widely used in anti-cancer chemotherapy is the group of anthracycline antibiotics which includes, inter alia, daunorubicin, doxorubicin (also known as Adriamycin® and doxorubicin hydrochloride), respinomycin D and idarubicin. These drugs interact with DNA by intercalation and inhibition of macromolecular biosynthesis thereby inhibiting the progression of the enzyme topoisomerase II, which unwinds DNA for transcription. They stabilize the topoisomerase II complex after it has broken the DNA chain for replication, preventing the DNA double helix from being resealed and thereby stopping the process of replication. It is commonly used in the treatment of a wide range of cancers.

Alkylating antineoplastic agents directly attack DNA. They attach an alkyl group to DNA, cross-linking guanine nucleobases in DNA double-helix strands. This makes the strands unable to uncoil and separate. As this is necessary in DNA replication, the cells can no longer divide. These drugs act nonspecifically. Cyclophosphamide is an alkylating agent, however, it is a highly potent immunosuppressive substance.

Topoisomerase I and II inhibitors interfere with the enzymatic activity of topoisomerase 1 and 2, respectively, eventually leading to inhibition of both DNA replication and transcription. Examples of topoisomerase I inhibitors include topotecan and irinotecan. Irinotecan, is a prodrug converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death. Because ongoing DNA synthesis is necessary for irinotecan to exert its cytotoxic effects, it is also classified as an S-phase-specific agent. Examples of topoisomerase II inhibitors include etoposide and teniposide.

Anti-angiogenic agents interfere with the generation of new blood vessels, eventually leading to the "starvation" of tumors. Non-limiting examples of anti-angiogenic agents include the monoclonal antibody bevacizumab, dopamine and tetrathiomolybdate.

Vascular endothelial growth factor (VEGF) is a 32-42 kDa dimeric glycoprotein which mediates vasodilatation, increased vascular permeability and endothelial cell mitogenesis. Differential exon splicing of the VEGF gene results in three main mRNA species which code for three secreted isoforms (subscripts denote numbers of amino acids): VEGF189, VEGF165, and VEGF121. A number of minor splice variants have also been described (VEGF206, VEGF183, VEGF145 and VEGF148). Variants of VEGF polypeptides and their use in cancer therapy is disclosed for example, in WO/2003/012105.

Combination Therapy with Radiation

According to various embodiments, the methods further comprise treating the subject with radiation. According to various embodiments, the methods comprise all of administering the antibody of the invention, administering the at least one chemotherapeutic agent and treating the subject with radiation. According to some embodiments, the antibody, the at least one chemotherapeutic agent and radiation treatment are administered substantially simultaneously, concurrently, alternately, successively or according to overlapping schedules.

The source of radiation that may be used in combination with the modified antibody of the invention and the chemotherapeutic agent(s) can be either external or internal to the patient being treated. When the source is external to the patient, the therapy is known as external beam radiation therapy (EBRT). When the source of radiation is internal to the patient, the treatment is called brachytherapy (BT).

Radiation is administered in accordance with well-known standard techniques using standard equipment manufactured for this purpose, such as AECL Theratron and Varian Clinac.

The distance between the source of the external radiation and the point of entry into the patient may be any distance that represents an acceptable balance between killing target cells and minimizing side effects. Typically, the source of the external radiation is between 70 and 100 cm from the point of entry into the patient.

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the invention is not limited to any particular dose. The dose will be determined by the treating physician in accordance with the particular factors in a given situation, including the factors mentioned above.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

Humanized Antibody of the Invention

As used herein, the terms "BAT" and a BAT antibody" are used in a broad sense and specifically cover antibodies identical to or based on the murine monoclonal antibody known as mBAT-1, or an antigen binding fragment thereof. The monoclonal antibody mBAT-1 is secreted by the hybridoma cell line deposited at the Collection Nationale de Cultures de Microorganismes (CNCM), under Accession No. 1-1397, as disclosed in U.S. Pat. No. 5,897,862. Further "BAT" and a BAT antibody" may refer to an antibody, which recognizes the same antigenic epitope as mBAT-1, for example a chimeric antibody as described in U.S. Patent Application Publication No. 2003/0026800. A BAT antibody also includes a humanized antibody, various examples of which are disclosed in WO03/099196 and U.S. Patent Application Publication No. 2008/0025980 and interchangeably denoted "CT-011", "hBAT" and "hBAT-1".

In general, the light chain variable region of the humanized monoclonal antibody is characterized by the formula:

$$FR_{L1}\text{-}CDR_{L1}\text{-}FR_{L2}\text{-}CDR_{L2}\text{-}FR_{L3}\text{-}CDR_{L3}\text{-}FR_{L4}$$

wherein each FR is independently a framework region of a human antibody and each CDR is independently a complementarity determining region of the monoclonal mBAT-1 antibody.

In general, the heavy chain variable region of the humanized monoclonal antibody is characterized by the formula:

$$FR_{H1}\text{-}CDR_{H1}\text{-}FR_{H2}\text{-}CDR_{H2}\text{-}FR_{H3}\text{-}CDR_{H3}\text{-}FR_{H4}$$

wherein each FR is independently a framework region of a human antibody and each CDR is independently a complementarity determining region of the monoclonal mBAT-1 antibody.

In particular embodiments, the FRs are derived from the light chain variable region of the human TEL9 antibody, or are modified therefrom in certain amino acid residues. Human TEL-9 antibody was identified in diverse libraries of immunoglobulin heavy (VH) and light (V kappa and V lambda) chain variable (V) genes prepared from peripheral blood lymphocytes of unimmunized donors (Marks et al. J Mol Biol. 1991, 222:581-97). This antibody was shown to bind specifically to the turkey egg-white lysozyme (TEL) antigen.

In particular embodiments, the FRs are derived from the heavy chain variable region of the human hsighv1295 antibody, or modified therefrom in certain amino acid residues. Human hsiggv1295 antibody was isolated from stable hybridomas and Epstein-Barr virus-transformed B cell lines from the synovial fluid or peripheral blood of three patients with rheumatoid arthritis and one patient with systemic lupus erythematosus (Fang et al., J Exp Med. 1994, 179:1445-56).

Compositions, Administration and Dosages

For use in the methods of the invention, the humanized antibody may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous intramuscular, subcutaneous, or intraperitoneal administration and conveniently comprise sterile aqueous solutions of the antibody, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with carriers, such as lactose, sucrose, starch, talc magnesium stearate, crystalline cellulose, methyl cellulose, carboxymethyl cellulose, glycerin, sodium alginate or gum arabic.

The humanized antibody of the invention is preferably administered parenterally, generally by intravenous infusion. Administration may also be by intraperitoneal, oral, subcutaneous, or intramuscular routes. Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric and humanized antibodies are expected to have circulatory half-lives of up to four and up to 14-21 days, respectively. In some cases it may be advantageous to administer a large loading dose followed by periodic (e.g., weekly) maintenance doses over the treatment period. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained.

Typically, the effective dose will be determined by the condition of the subject, as well as the body weight or surface area of the subject to be treated. The size of the dose and the dosing regimen also will be determined by the existence, nature, and extent of any adverse side effects that accompany the administration of modified antibodies of the invention in a particular subject. In determining the effective amount of the therapeutic composition to be administered, the physician needs to evaluate inter alia circulating plasma levels, toxicity, and progression of the disease.

The term "effective amount" with respect to the humanized antibody and the chemotherapeutic agent(s) of the invention should be understood as meaning an amount of each of these active agents required to achieve a therapeutic effect, without causing excessive or uncontrollable adverse side effects. The effective amount required to achieve the therapeutic end result may depend on a number of factors including, for example, the specific type of the tumor and the severity of the patient's condition, and whether the combination is further co-administered with radiation. The effective amount (dose) of the active agents, in the context of the present invention should be sufficient to effect a beneficial therapeutic response in the subject over time, including inhibition of tumor growth, reduction in the rate of tumor growth, prevention of tumor and metastasis growth and enhanced survival.

In various embodiments of the combination methods of the invention, the antibody and the chemotherapeutic agent may be administered according to any of a number of treatment schedules, also referred to "dosing schedules" and "administration regimens", referring to the frequency of administration and order of administration of each active agent. For example, the antibody and the chemotherapeutic agent may be administered substantially simultaneously i.e. at the same time, using for example a combined dosage form or separate dosage forms. This form of administration may also be referred to as "concomitant" administration. Concurrent administration refers to administration of the active agents within the same general time period, for example on the same day(s) but not necessarily at the same time. For example, one active agent may require administration with food, while the other requires administration in the semi-fasting state. Alternate administration includes administration of one agent during a particular time period, for example over the course of a few days or a week, followed by administration of the other agent during a subsequent identical period of time, and then repeating the pattern for one or more cycles. Sequential or successive administration includes administration of one agent during a first time period, using one or more doses, followed by administration of the other agent during a second time period using one or more doses. An overlapping schedule may also be employed, which includes administration of the active agents on different days over the treatment period, not necessarily according to a regular sequence. Variations on these general guidelines may also be employed, according to the agents used and the condition of the subject.

In some particular combinations, it may be advantageous to use a specific sequence of administration e.g. one agent prior to the other.

Having now generally described the invention, the same will be more readily understood through reference to the following examples, which are provided by way of illustration and are not intended to be limiting of the present invention.

EXAMPLES

Example 1

CD4+ T Lymphocytes Viability Following Incubation with a CT-011 Double Mutant

A CT-011 double mutant antibody comprising amino acid substitutions of Trp 107 to Ala and Phe 97 to Ala was formed (denoted w222+F97). Representative example of 48 hours activated human CD4+ T lymphocytes incubated with 1 ug/ml or 0.1 ug/ml CT-011 or CT-011 double mutant W222+F97 or isotype control antibody for additional 72 hours. Cell viability was evaluated by Trypan Blue exclusion.

As seen in FIG. 1, lymphocyte viability is higher at the cultures including the double mutant antibody. Y-axis of FIG. 1 indicates concentration of viable cells.

Example 2

In Vivo Effect of the Modified hBAT-1 in a Murine Tumor Model

To examine whether the modified antibodies of the present invention can transmit the biological effects characteristic of mBAT-1 or hBAT-1, the efficacy of the modified antibodies is studied in vivo.

C57BL mice are inoculated with B16 melanoma cells to induce lung metastases. Increasing amounts (1, 10 and 20 µg) of a modified mAb of the invention is injected on day 12 post tumor-inoculation and compared to an optimal dose of 10 µg mBAT-1 and/or hBAT-1. Lung weight may be measured on Day 24 post tumor inoculation to indicate the establishment of a tumor. The average lung weight per treatment is indicative of the various tested mAbs.

Example 3

Inhibition of Human Melanoma (SK-28) in SCID Mice by the Modified hBAT-1

Mouse and human BAT-1 mAb have been shown to inhibit the formation of human-tumor metastases in the presence of human peripheral blood lymphocytes (hPBL). To estimate the efficacy of modified hBAT-1 in inhibition of human cancer, the modified antibody is studied in a model combining both tumors and lymphocytes of human origin. Severe combined immune-deficient mice (SCID) is engrafted with hPBL to restore immune-competence. Mice are challenged with human melanoma cells (SK-28) and treated with increasing concentrations of the humanized antibody, administered in a single i.v. dose on day 11 post tumor inoculation.

Example 4

Immunotherapy of Human Colorectal Cancer Hepatic Metastases by the Modified hBAT-1 mAb in Nude Mice LIM6 and HM7 are two sub-clones of the human CRC cell line LS174T that were selected for their high mucin synthesis and metastatic potential. The tumor cells are injected into the exposed spleen of anesthetized nude mice. After 1 minute, the spleens are removed and the excisions closed. Low doses of mBAT-1, hBAT-1 and modified hBAT-1 antibodies of the invention are administered 12 days later and mice are sacrificed 35 days post tumor inoculation. The livers are weighed, the number of metastatic nodules counted, and liver tissue processed for histology and Immunohistochemistry study.

Example 5

Co-Localization of the Modified hBAT with CD4 and CD8

Mouse and human BAT-1 have been shown to bind human lymphocytes, recognizing both CD4+ and CD8+ subsets. To establish the binding specificity of the modified humanized mAbs of the invention, human Peripheral Blood Lymphocytes (PBL) are isolated from the blood of normal donors, as described hereinbelow, and analyzed for co-localization of hBAT with known lymphocyte markers.

Peripheral blood mononuclear cells (PBMC) are isolated by ficoll and incubated in tissue culture plates to remove adherent cells. Isolated are were gated on lymphocytes by size and granularity and on live cells by propidium iodine (PI) exclusion. Binding is performed at 4° C. for 1 hr, and determined by flow cytometry on gated lymphocytes.

Example 6

Binding of the Modified hBAT-1 to B Lymphocytes

The modified humanized mAb of the invention are raised against the membranes of Daudi cells, a human B lymphoma cell-line. PBL from normal donors are isolated by ficoll, as known in the art, followed by adherence to tissue culture plates. Non-adherent cells are examined for the co-localization of the antibodies with B-cell markers including CD19 and CD20. Binding is performed at 4° C. for 1 hr, and determined by flow cytometry on gated lymphocytes.

Example 7

Stability of the Modified hBAT-1

CT-001 mAbs comprising at least one amino acid modification in a position selected from: Thr 5, Thr 20, Cys 71, Asn 75, Ser 76, Phe 93 and Phe 97 of the light chain variable region having the amino acid sequence of SEQ ID NO: 1-4; Asp 54, Ser 55 and Trp 107 of the heavy chain variable region having the amino acid sequence of SEQ ID NO: 5-9; Asn 51, Ser 52, Asp 63 and Ser 64 of the light chain constant region having the amino acid sequence of SEQ ID NO: 10; or Thr 3, Ser 7, Asn 42, Ser 43, Asn 86, His 87, Asp 104, Lys 105, Thr 108, Met 135, Asp 153, Pro 154, Asp 163, Gly 164, Asn 180, Ser 181, Asn 198, Gly 199, Asn 267, Gly 268, Asp 282, Ser 283, Asp 284, Ser 285, Asn 317, His 318, Lys 330 and Met 311 of the heavy chain constant region having the amino acid sequence of SEQ ID NO: 12, are formed as known in the art.

The stability of the modified mAbs is evaluated using various biochemical and biophysical techniques that assess size, aggregation state, structure, and intermolecular contacts of the antibodies as known in the art. For instance, the purity and aggregation state of the antibodies may be studied by size exclusion chromatography (SEC) and analytical ultracentrifugation (AUC).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. An isolated anti-BAT antibody or antigen binding fragment thereof comprising a light chain variable region set forth in SEQ ID NO: 1 wherein Phe 97 is substituted with Ala, and a heavy chain variable region set forth in SEQ ID NO: 5 wherein Trp 107 is substituted with Ala.

2. The isolated antibody or antigen binding fragment thereof of claim 1, wherein the fragment is selected from the group consisting of: Fv, F (ab'), F (ab') 2, and a single chain antibody.

3. A pharmaceutical composition comprising as an active ingredient the isolated antibody of claim 1 or an antigen binding fragment thereof, and a pharmaceutically acceptable carrier, diluent or stabilizer.

* * * * *